United States Patent [19]

Chen et al.

[11] 4,167,638

[45] Sep. 11, 1979

[54] PROCESS FOR PRODUCTION OF 8-NHR QUINOLINES

[75] Inventors: Eugene H. Chen, Marlton, N.J.; Andrew J. Saggiomo; Edward A. Nodiff, both of Philadelphia, Pa.

[73] Assignee: The United States of America as represented by the Secretary of the Army, Washington, D.C.

[21] Appl. No.: 774,165

[22] Filed: Mar. 3, 1977

[51] Int. Cl.² ............................................. C07D 215/40
[52] U.S. Cl. ..................................... 546/171; 542/455; 546/153; 546/157; 546/159; 546/83
[58] Field of Search ........ 260/288 CE, 288 A, 288 R; 546/83, 153, 157, 171

[56] References Cited

U.S. PATENT DOCUMENTS

| 2,508,937 | 5/1950 | Campbell | 260/286 |
| 2,852,518 | 9/1958 | Morgan et al. | 260/286 |

FOREIGN PATENT DOCUMENTS

| 589152 | 6/1947 | United Kingdom . |
| 826811 | 1/1960 | United Kingdom . |
| 931574 | 7/1963 | United Kingdom . |
| 991509 | 5/1965 | United Kingdom . |

OTHER PUBLICATIONS

Shetty et al., J. Med. Chem. 20, 1349–1351, (1977).
Shetty et al., J. Med. Chem. 21, 995–998, (1978).
Montagne et al., J. Med. Chem. 20, 1122–1127, (1977).
Chen et al., J. Med. Chem. 20, 1107–1109, (1977).

*Primary Examiner*—Donald G. Daus
*Assistant Examiner*—Diana G. Rivers
*Attorney, Agent, or Firm*—William G. Gapcynski; Werten F. W. Bellamy; Sherman D. Winters

[57] ABSTRACT

An improved process for producing 8-NHR quinolines from 8-aminoquinolines is disclosed. The process comprises reacting 8-aminoquinolines with a substituted alkyl halide in the presence of an amine having a boiling point of 80°–90° C. The amine functions as an acid acceptor whereby the amine salt formed may be efficiently separated from the 8-NHR quinoline formed without expensive or time consuming purification steps. The reaction may be carried out in the presence of a solvent such as an alcohol.

10 Claims, No Drawings

PROCESS FOR PRODUCTION OF 8-NHR QUINOLINES

BACKGROUND OF INVENTION

Compounds broadly identified as 8-NHR quinolines are well known as valuable anti-parasitic agents in clinical medicine and are specifically used in the treatment of conditions resulting from the presence in the blood and tissues of parasites. See, Reduced 8-Aminoquinoline Analogs As Potential Anti-malarial Agents, Carrol et al., J. of Md. Chem. 19, 1111 (1976).

Considerable difficulty however, has been experienced in the past in synthesizing specific compounds or in purifying a compound to produce these quinolines in pharmaceutically acceptable forms. For example, one synthesis procedure uses two equivalents of an 8-$NH_2$ quinoline in a reaction with a substituted alkyl halide (hereinafter RX). In this reaction one equivalent is consumed in taking up the acid (HX) liberated in the reaction. In this instance then the 8-NHR quinoline products must be purified, and the starting material 8-$NH_2$ quinoline must be recovered. Both purification of the product, and recovery of the starting material involve costly skilled labor and are time consuming.

Other means for synthesis of the 8-NHR quinolines give lower yields than the foregoing process, or less product, or both, and are often accompanied by a product that is difficult to purify. The process of this invention, however, for the synthesis of 8-NHR quinolines has been found to be broadly applicable to a wide variety of such compounds, and provides a good quality product in satisfactory yields.

The process of this invention to produce 8 amino quinoline derivatives involves the discovery that if a basically substituted halide (RX) is reacted with 8-$NH_2$ quinoline in the presence of an acid acceptor such as an amine, the requisite side chain will be added to form 8-NHR quinoline and the acid acceptor will form an amine salt which may be readily separated from the pure product.

The present invention, then, consists in the interaction of 8-aminoquinoline compounds with RX, a substituted alkyl halide, in the presence of an amine as an acid acceptor. Suitable amines having boiling points in the range of 80°-90° include triethylamine and diisopropylamine, and from the standpoint of broadest applicability, triethylamine is preferred. The acid acceptor, then, facilitates the reaction and simplifies purification of the product. The process of this invention, then, provides 8-NHR quinoline chemotherapeutic agents at decreased cost of production. Moreover, the instant method renders accessible a variety of 8-NHR quinolines of diverse structural types in good yield. In most cases the compounds formed are of a purity adequate for ready formation of pharmaceutically acceptable salts.

The reaction may be carried out in the presence of an alcohol solvent such as ethanol or 2-ethoxyethanol as a reaction medium. It has been discovered that such alcohols facilitate the interaction of the 8-$NH_2$ quinoline with the RX in the presence of the amine acid acceptor. In certain instances, reagents are heated together without solvent at temperatures in the range of 100°-175° C. Upon completion of the reaction the HX salt of the acid acceptor is removed as will be hereinafter described.

The 8-NHR quinoline compound formed by the reaction of this invention may be the desired drug itself, or an intermediate from which a desired drug may be formed. Therefore the general freedom from contaminants in the product is of practical importance whether the product is the end result or an intermediate. In the former instance, direct formation of a pharmaceutically acceptable salt from the product is facilitated, and in the latter, clean conversion to requisite products does not demand tedious purification of intermediates.

Accordingly, it is an object of this invention to provide a new process for producing chemotherapeutic agents in high yields and of high purity.

It is another object to provide a process for forming alkyl substituted quinoline compounds useful as chemotherapeutic agents or as intermediates for the formation of chemotherapeutic agents from a 8-aminoquinolines.

It is still another object to provide an efficient process for producing 8-amino substituted quinolines by reacting 8-aminoquinolines with the desired substituent alkyl halide in the presence of an amine which acts as an acid acceptor to provide a product which may be readily separated from the amine acid salt formed as a by-product.

It is still another object of this invention to provide a process for producing a wide variety of structurally related 8-NHR quinolines which process is both efficient and adaptable to a wide variety of starting materials consisting of reacting 8-aminoquinoline with an alkyl halide in the presence of an amine having a boiling point in the range of 80°-90° C. to form said product and an amine salt.

These and other objects will become readily apparent with reference to the following description and examples.

The following are specific examples of the process of this invention synthesizing diverse 8-NHR quinolines, which examples illustrate the broad applicability of the process of this invention. The following examples illustrate both formation of the 8-NHR quinolines, a pharmaceutically acceptable salt thereof, or use of the product formed as an intermediate to form a more valuable derivative. As such, the examples are intended to be illustrative and not limiting the scope of the instant invention.

As described above, the instant invention is based upon the interaction of 8-$NH_2$ quinoline type compounds with a substituted alkyl halide (RX) in the presence of a suitable amine such as triethylamine or diisopropylamine. The HX salt of the amine formed by the reaction is then separated and the 8-NHR quinoline obtained for direct use, or conversion to a pharmaceutically acceptable salt for therapeutic application, or for transformation into another 8-NHR quinoline of greater chemotherapeutic worth. In the following examples all temperatures are specified as degrees Celsius.

EXAMPLES

EXAMPLE 1.

8-(4-Aminopentylamino)-6-methoxyquinoline

A. 1-Iodo-4-Phthalimidopentane

3-Acetyl-1-propanol was converted (99% yield) into 4-amino-1-pentanol by hydrogenation at 3 atm. pressure in aqueous ammonia in the presence of Raney nickel catalyst. 4-Phthalimido-1-pentanol was obtained in 84% yield by reaction of 4-amino-1-pentanol with phthalic anhydride in boiling xylene. 1-Chloro-4-phthalimidopentane was produced (83% yield) by the action of thionyl chloride on 4-phthalimido-1-pentanol in benzene solution. The chloro compound was converted into the requisite 1-iodo-4-phthalimidopentane in 68% crude yield by interchange with sodium iodide in boiling acetone. It could be used directly in the reaction with 8amino-6-methoxyquinoline, however it was readily obtained as a colorless oil, b.p. 174°–178° (1.5 mm)

Anal. Calcd. for $C_{13}H_{14}INO_2$: C, 45.48; H, 4.11; N, 4.08. Found: C, 45.45; H, 3.97; N, 4.05.

B. 6-Methoxy-8-(4-phthalimidopentylamino) quinoline hydrochloride.

A stirred mixture of 84.0 g (0.245 mole) of 1-iodo-4-phthalimidopentane and 42.7 g (0.245 mole) of 8-amino-6-methoxyquinoline (freshly distilled) was maintained at 150° while 24.8 g of triethylamine was added in portions during 15 min. Stirring was continued at 150° for 1 hr and an additional 12.2 g of 1-iodo-4-phthalimidopentane and 6.15 g of triethylamine (dropwise during 10 min) were introduced. After an additional 2.5 hr at 150°, the reaction mixture was cooled and diluted with acetone. The solution was treated with carbon and the acetone removed. The residue was extracted with warm ether (6 l.), leaving a purple solid; the ether was removed in vacuo. The residue was dissolved in 100 ml of methanol and then 85 g of a 10% solution of hydrogen chloride in methanol was added and the mixture was stirred overnight. The precipitated orange salt was washed with methanol, and recrystallized from methanol to yield 28.8 g of orange solid mp 137°–143°, and a second crop of 11.8 g, mp 108°–125°; total yield 39%.

C. 8-(4-Aminopentylamino)-6-methoxyquinoline phosphate (Quinocide monophosphate).

A mixture of 40.6 g (0.096 mole) of 6-methoxy-8-(4-phthalimidopentylamino) quinoline hydrochloride and 11.0 g of hydrazine hydrate in 400 ml of ethanol was heated under reflux for 5 hr, cooled and filtered to remove phthalhydrazide. The ethanolic filtrate was evaporated to dryness in vacuo; 200 ml of benzene and 240 ml of 35% aqueous potassium hydroxide were added to the residue and the mixture was stirred at 40°14 50° for 30 min. The benzene layer was separated, and the aqueous alkaline layer was extracted with additional benzene (4×50 ml). The benzene layer was washed with water (2×50 ml), decolorized with carbon, concentrated, and the residue distilled to give 14.7 g (60%) of yellow oil, bp 161°–180°/0.3–0.5 mm, which solidified on standing, mp 42°–47°.

A vigorously stirred solution of 11.8 g (0.0456 mole) of N'-(6-methoxy-8-quinolinyl)-1,4-pentanediamine base in 1450 ml of ether was treated dropwise over 1.5 hr, with 10.4 g of 86% phosphoric acid in 52 ml of ethanol. The resulting yellow suspension was stirred at room temperature for 1.5 hr, heated under reflux for 3 hr, and stirred at room temperature overnight. The yellow solid was collected and sequentially washed with ethanol and ether to give 20.3 g of product, mp 140°–150°. The solid was recrystallized from a methanol-ethanol mixture to yield 10.2 g (63%) of the monophosphate salt, mp 188.5° (dec).

Anal. Calcd. for $C_{15}H_{21}N_3O \cdot H_3PO_4$: C, 50.42; H, 6.77; N, 11.75. Found: C, 50.38; H, 6.82; N, 11.73.

The filtrate from the recrystallization was concentrated in vacuo and recrystallized from methanol to yield 6.3 g of a yellow solid. That analyzed as a mixture of the di- and triphosphate salts of the base.

EXAMPLE 2.
8-(4-Aminopentylamino)-6-methoxy-2-methylquinoline

A. 6-Methoxy-2-methyl-8-(4-phthalimidopentylamino) quinoline hydrochloride.

A stirred mixture of 3.8 g (0.02 mole) of 8-amino-6-methoxy-2-methylquinoline and 7 g (0.02 mole) of 1-iodo-4-phthalimido pentane was maintained at 150° while 2 g (0.02 mole) of triethylamine was added in portions during 10 min. Stirring was continued at 150° for 30 min and an additional 1.5 g of iodo compound (single portion) and 1 g of triethylamine (dropwise during 10 min) were introduced. After 15 more min at 150°, the reaction mixture was allowed to cool and diluted with acetone. The solution was treated with carbon and the acetone was removed under reduced pressure. The residue was extracted with warm ether (400 ml) and the cooled extract was slowly treated with ethereal hydrogen chloride to give a small amount of dark solid (discarded) and then 9.8 g of orange product. This material was thoroughly washed with methanol-ether (1:4) and then with pure ether to give 6.2 g (71%) of hydrochloride, mp 199°–204°.

Anal. Calcd. for $C_{24}H_{26}ClN_3O_3$: C, 65.52; H, 5.94; N, 9.55. Found: C, 65.28; H, 5.99; N, 9.27.

Phthalimido alkylation with 1-chloro-4-phthalimidopentane, instead of with iodo compound, provided essentially the same yield of product (76%) but required 9 hr reaction time.

B. 8-(4-Aminopentylamino)-6-methoxy-2-methylquinoline diphosphate.

A stirred slurry of 16 g (0.037 mole) of 6-methoxy-2-methyl-8-(4-phthalimidopentylamino) quinoline hydrochoride and 500 ml of ether was treated, at room temperature, with 6 g of triethylamine. Filtration of triethylamine hydrochloride, vacuum removal of ether and excess triethylamine and trituration of the residue with petroleum ether provided 14 g (98%) of the free base of the phthalimido compound as a pale yellow powder, mp 99°–101°. A mixture of this base (14 g, 0.035 mole), 95% hydrazine (15 ml) and ethanol (550 ml) was heated under reflux for 30 hr and cooled. The mixture was filtered to remove phthalhydrazide and the filtrate was concentrated in vacuo. The residue was extracted with warm ether (600 ml) and the extract was filtered, washed with 30% KOH (3×100 ml) and water (3×50 ml) and then extracted with 20% HCl (3×50 ml) and water (2×50 ml). The combined HCl and aqueous extracts were washed with ether (2×50 ml), basified with 30% NaOH and extracted with ether. The extract was dried (MgSO4) and treated with 65% $H_3PO_4$ in methanol to give 15 g (91%) of the diphosphate as a yellow solid, mp 204°–206°. Washing with 20% methanol in ether and then with pure ether provided the analytical sample, mp 204°–206°.

Anal. Calcd. for $C_{16}H_{24}N_3O \cdot 2H_2O$: C, 39.43; H, 6.41; N, 8.62. Found: C, 39.77; H, 6.24; N, 8.55.

EXAMPLE 3.
8-(4-Aminopentylamino)-6-methoxy-4-methylquinoline

A. 6-Methoxy-4-methyl-8-(4-phthalimidopentylamino) quinoline.

METHOD A

A stirred mixture of 7.6 g (0.04 mole) of 8-amino-6-methoxy-4-methylquinoline and 14 g (0.04 mole) of 1-iodo-4-phthalimidopentane was maintained at 150° while 5 g (0.04 mole) of triethylamine was added in portions during 15 min. Stirring was continued at 150° for 0.5 hr. (almost all quinoline intermediate consumed, according to tlc) and an additional 4 g of iodo intermediate (single portion) and 1 g of triethylamine (dropwise during 10 min) were introduced. After 2 more hours at 150°, the reaction mixture was cooled and diluted with acetone. The solution was treated with carbon and the acetone was removed. The residue was extracted with warm ether (700 ml) and the cooled extract was slowly treated with ethereal hydrogen chloride to give about 1 g of pale yellow solid (discarded) and then 17.5 g of orange product (as the hydrochloride). Trituration of this material with methanol-ether (1:2) provided 15.5 g (88%) of product, mp 165°-175°. An analytical sample mp 182°-184°, was obtained by crystallizing twice from methanol and hydrating by exposure to moist air.

Anal. Calcd. for $C_{24}H_{25}N_3O_3 \cdot HCl \cdot H_2O$: C, 62.93; H, 6.16; N, 9.18. Found: C, 62.30; H, 6.10; N, 8.97.

The hydrochloride (19 g) was slurried in ether, treated with triethylamine (10 ml), filtered and concentrated to give 16.7 g of free base as a tan oil. The latter was used in the next step without further purification.

METHOD B

A stirred mixture of 8-amino-6-methoxy-4-methylquinoline (3.8 g, 0.02 mole) and 1-chloro-4-phthalimidopentane (5 g, 0.02 mole) was heated at 150° while triethylamine (2 g) was added, in portions, during 2 hr. After stirring at 150° for two more hours, tlc indicated that about half of the starting material was still unreacted. An additional 5 g of 1-chloro-4-phthalimidopentane was added in a single portion and 2 g of triethylamine was added during 2 hr as described above. The reaction was maintained at 150° until the 8-aminoquinoline type was no longer evident (4 hr), cooled and diluted with acetone. The precipitated triethylamine hydrochloride was removed and the filtrate was treated with carbon and concentrated to dryness. The residue was extracted with 400 ml of ether and treated with ethereal HCl as described in Method A to give 7.5 g (85%) of hydrochloride, mp 176°-180°.

The infrared spectra of samples of hydrochlorides, obtained via methods A and B, were identical.

B.
8-(4-Aminopentylamino)-6-methoxy-4-methylquinoline.

A stirred mixture of 6-methoxy-4-methyl-8-(4-phthalimidopentylamino) quinoline base (16.7 g, 0.041 mole), 95% hydrazine (17 g) and ethanol (450 ml) was heated under reflux for 5 hr, cooled and filtered to remove phthalhydrazide. The filtrate was evaporated to dryness in vacuo and the residue was extracted with 400 ml of ether. The filtered extract was washed with 30% potassium hydroxide (3×100 ml) and water (3×50 ml) and then extracted with 20% HCl (2×100 ml) and water (2×50 ml, discarded) and basified with 30% NaOH solution. The basic mixture was extracted with ether and the extract was dried over anhydrous magnesium sulfate and concentrated to give 10 g (89%) of base as a tan oil which solidified on standing. Distillation of this material (bp 174°-176°/1 mm) provided pure base as a white solid, mp 57°-14 58.5°.

Anal. Calcd. for $C_{16}H_{23}N_3O$: C, 70.29; H, 8.48; N, 15.37. Found: C, 70.54; H, 8.45; N, 15.08.

A vigorously stirred solution of 2.5 g (0.0092 mole) of the above base in 300 ml of ether was treated, dropwise, with 2 g of 86% phosphoric acid in 10 ml of ethanol. The resulting yellow suspension was stirred for an hour, allowed to stand overnight and filtered. The yellow solid was sequentially washed with a little ethanol and ether and crystallized from methanol to give 3.5 g (82%) of 8-(4-aminopentylamino)-6-methoxy-4-methylquinoline diphosphate as a yellow solid, mp 187°-189°.

Anal. Calcd. for $C_{16}H_{23}N_3O \cdot 2H_3PO_4$: C, 40.94; H, 6.23; N, 8.95. Found: C, 41.14; H, 6.28; N, 8.70.

EXAMPLE 4.
8-(4-Amino-1-metylbutylamino)-6-methoxy-3-methylquinoline

A. 8-Amino-6-methoxy-3-methylquinoline.

4-Amino-3-nitroanisole was subjected to a Skraup reaction with 90% methacrolein at 110° to afford a 50% yield of 6-methoxy-3-methyl-8-nitroquinoline. The compound crystallized from ethyl acetate as a yellow solid, mp 173°-175°.

Reduction of the foregoing nitro compound to 8-amino-6-methoxy-3-methylquinoline in a hot mixture of di-n-butyl ether and dilute acetic acid was accomplished by addition of iron filings. The crude product was recrystallized from ligroin to afford pure compound as short, pale yellow needles which melted 94.5°-96°.

B.
6-Methoxy-3-methyl-8-(1-methyl-4-phthalimidobutylamino) quinoline hydrochloride.

A stirred mixture of 8-amino-6-methoxy-3-methylquinoline (7.5 g, 0.04 mole) and 4-bromo-1-phthalimidopentane (15 g 0.05 mole) was maintained at 140° while triethylamine (5.4 g, 0.054 mole) was added in portions during 2 hr. The mixture was kept at 140° for two more hrs and two additional portions of bromide (12 g, 0.04 mole) and triethylamine (4.2 g) were introduced in a similar manner at 4 hr intervals. The mixture was cooled, diluted with acetone (100 ml) and an almost quantitative yield of triethylamine hydrobromide was filtered. The filtrate was treated with charcoal and concentrated to dryness in vacuo. The residue was extracted with warm ether (300 ml) and the extract was treated dropwise with ethereal HCl. A number of brown fractions were initially separated and then continued addition of ether-HCl gave 15 g of the hydrochloride of the desired compound as orange solid, mp 172°-177°. This material was triturated with a small amount of methanol, slurried with ether and crystallized from methanol to give 12 g (68%) of product, mp 189°-191°. This material was basified with conc NH$_4$OH and the free base was crystallized twice from methanol (charcoal) to give 9.5 g (60%) of base, mp 94°-97°.

Anal. Calcd. for $C_{24}H_{25}N_3O_3$: C, 71.45; H, 6.24; N, 10.42. Found: C, 71.40; H, 6.08; N, 10.26.

C.
8-(4-Amino-1-methylbutylamino)-6-methoxy-3-methylquinoline

A stirred mixture of 6-methoxy-3-methyl-8-(1-methyl-4-phthalimido-butylamino) quinoline (8 g, 0.02 mole), 95% hydrazine (10 ml) and 350 ml of ethanol was heated under reflux for 10 hr and allowed to cool overnight. An almost quantitative yield of phthalhydrazide was filtered and the filtrate was concentrated to dryness in vacuo. The pale yellow residue was extracted with warm ether and the extract was washed with 30% KOH (3×100 ml) and water (4×100 ml) and dried (MgSO$_4$). Slow addition of the extract to ether-HCl gave an orange yellow solid which, on washing with ether and acetone provided 5 g (73%) of 6-methoxy-3-methyl-8-(4-amino-1-methylbutylamino) quinoline dihydrochloride, mp 210°-211°.

Anal. Calcd. for C$_{16}$H$_{23}$N$_3$O·2HCl: C, 55.46; H, 7.27; N, 12.13. Found: C, 55.73; H, 7.33; N, 12.05.

EXAMPLE 5.
8-(4-Amino-1-methylbutylamino)-6-methoxy-2-trifluoromethyl quinoline A. 8-Amino-6-methoxy-2-trifluromethylquinoline.

The reaction of 4-methoxy-2-nitroaniline with ethyl trifluoroacetoacetate in polyphosphoric acid at 130°-140° gave 4-hydroxy-6-methoxy-8-nitro-2-trifluoromethylquinoline. The pure compound (tan crystals, mp 138°-140°) was obtained in 27% yield following several crystallizations of the crude product from ligroin.

The foregoing 4-hydroxy-compound was converted into 4-chloro-6-methoxy-8-nitro-2-trifluoromethylquinoline by the action of a refluxing mixture of phosphorus oxychloride and phosphorus pentachloride. It separated from ethanol (93% yield of product) as yellow needles, mp 147°-149°.

A mixture of 3.1 g of (0.01 mole) of 4-chloro-6-methoxy-8-nitro-2-trifluoromethylquinoline, 75 ml of ethanol and 1 g of 5% Pd on CaCO$_3$ was shaken on a Parr apparatus for 4.5 hr, at 50°-60°, under a hydrogen pressure of 70 psig. The yellow mixture was filtered and concentrated to dryness in vacuo. The residue was extracted with boiling ligroine (bp 90°-120°) and the solvent was removed from the extract under reduced pressure. The residue was distilled to give 1.25 g (52%) of 8-amino-6-methoxy-2-trifluoromethylquinoline as a yellow oil, bp 127°-128°/1 mm.

Anal. Calcd. for C$_{11}$H$_9$F$_3$N$_2$O: C, 54.55; H, 3.74; N, 11.57. Found: C, 54.87; H, 3.92; N, 11.41.

B.
6-Methoxy-8-(1-methyl-4-phthalimidobutylamino)-6-trifluoromethylquinoline.

A stirred mixture of 8-amino-6-methoxy-2-trifluoromethylquinoline (2.4 g, 0.01 mole) and 4-bromo-1-phthalimidopentane (3.6 g, 0.012 mole) was heated at 150°-155° while triethylamine (1.4 g, 0.014 mole) was added, dropwise, during 2 hr. The resulting orange suspension was heated for an additional 2 hr, at 150°-155°, and the reaction was then continued, at 158°-160°, according to a schedule of incremental addition of bromo compound (7.2 g) and triethylamine (2.8 g) during 12 hr. Thereafter, it was heated at ca. 160° for 4 hr and then allowed to cool.

To the cooled, orange, viscous reaction mixture was added 75 ml acetone. The precipitated crude yellow-white triethylamine hydrobromide (7 g) was filtered and the yellow filtrate was evaporated, in vacuo, to leave an orange-brown viscous residue. The residue was triturated with ether and an additional small amount of triethylamine hydrobromide was filtered. The yellow filtrate was treated, dropwise, with ethereal hydrogen chloride (ca. 15 ml) and a brown hygroscopic precipitate of brown solid was removed. Continued additional of ether-HCl (excess) provided more hydrochloride of product as a yellow hygroscopic solid which tended to darken on drying in air. The combined brown and yellow fractions of the hydrochloride were treated with excess 10% NH$_4$OH and the resulting free base was extracted with ether. The extract was dried (Drierite), evaporated, in vacuo, to dryness and the orange-brown, glassy residue was pumped at 55°-60° (0.5 mm) for 0.5 hr. Trituration of the residue with ether gave 0.9 g of yellow solid, mp 122°-123.5°. The latter was washed, on the funnel, with 1:1 ether-pet ether (bp 20°-40°) and then with pure pet ether. On standing, the combined washings deposited 0.45 g of 6-methoxy-8-(1-methyl-4-phthalimidobutylamino)-2-trifluoromethylquinoline for a combined weight of 1.35 g (30%). Crystallization from hexane provided an analytical sample as microscopic yellow needles, mp 125.5°-126.5°.

Anal. Calcd. for C$_{24}$H$_{22}$F$_3$N$_3$O$_3$: C, 63.01; H, 4.85; N, 9.19. Found: C, 62.58; H, 4.95; N, 8.81.

C.
8-(4-Amino-1-methylbutylamino)-6-methoxy-2-trifluoromethylquinoline.

A solution of 3.92 g (0.0085 mole) of 6-methoxy-8-(1-methyl-4-phthalimidobutylamino)-2-trifluoromethylquinoline, 5.2 ml of 95% hydrazine, 180 ml of ethanol and 108 ml of chloroform was heated under reflux for 6 hr, allowed to cool overnight and filtered to remove a quantitative yield of phthalhydrazide. The filtrate was brought to dryness, in vacuo, and the residual "mush" was extracted with boiling pet ether (2×150 ml). The combined, filtered extracts were diluted with ether (300 ml), washed with 30% KOH (2×50 ml) and water (4×50 ml) and re-filtered. Solvent was removed by bubbling pre-purified nitrogen through the solution for one day. The residual yellow oil was dissolved in 100 ml of methanol, treated with carbon and then with a solution of 3 g (0.026 mole) of 85% H$_3$PO$_4$ in 5 ml of methanol. The mixture was brought to dryness under reduced pressure and the tan solid was dried, in a vacuum, at 70°, for 4 hr. Repeated washing, in a mortar, with ether afforded 5.2 g of crude product. This material was combined with 0.8 g of product, obtained from a previous run, and dissolved, under nitrogen, in 60 ml of refluxing 2-propanol. The yellow solution was allowed to cool slowly to 5° and the crystalline yellow solid was vacuum-dried for 2.5 hr at 50°; yield 3.85 g; mp, indefinite, 120°-190°. The solid was treated with 50 ml of boiling 2-propanol and the mixture was allowed to cool to room temperature to give 3.45 g (combined yield, 78%) of 8-(4-amino-1-methylbutylamino)-6-methoxy-2-trifluoromethylquinoline monophosphate, mp 190°-192° (dec).

Anal. Calcd. for C$_{16}$H$_{20}$F$_3$N$_3$O·H$_3$PO$_4$: C, 45.18; H, 5.45; N. 9.88. Found: C, 45.45; H, 5.57; N, 9.87.

EXAMPLE 6.
8-(4-Amino-1-methylbutylamino)-6-methoxy-4-(3-trifluoromethylstyryl) quinoline A.
8-Amino-6-methoxy-4-(3-trifluoromethylstyryl)quinoline.

A stirred mixture of 6-methoxy-4-methyl-8-nitroquinoline (5.45 g; 0.24 mole) and 3-trifluoromethyl benzaldehyde (16.72 g; 0.096 mole), and anhydrous sodium acetate (0.66 g; 0.008 mole) was heated in an oil bath at 175°-180° for 10 hr. The mixture was allowed to cool, poured into ice water, rendered alkaline with sodium carbonate, and extracted with chloroform. The extracts were dried over anhydrous potassium carbonate, charcoaled, filtered, and the solvent removed in vacuo. The residual solid was crystallized several times from methanol (charcoal) to give a 59% yield of the pale yellow crystals, mp 144°–145°. This was 6-methoxy-8-nitro-4-(3-trifluoromethylstyryl)quinoline.

Anal. Calcd. for $C_{19}H_{13}F_3N_2O_3$: C, 60.95; H, 3.50; N, 7.50. Found: C, 60.96; H, 3.50; N, 7.29.

The foregoing nitro compound was reduced after the manner described in Example 4a. The crude product was recrystallized from aqueous methanol to obtain 8-amino-6-methoxy-4-(3-trifluoromethylstyryl) quinoline as a crystalline solid, mp 124°–126°. A 55% yield resulted.

Anal. Calcd. for $C_{19}H_{15}F_3N_2O$: C, 66.27; H, 4.40; N, 8.14. Found: C, 66.41; H, 4.38; N, 7.94.

B.
6-Methoxy-8-(1-methyl-4-phthalimidobutylamino)-4-(3-trifluoromethylstyryl)quinoline.

A mixture of 8.4 g (0.025 mole) of 8-amino-6-methoxy-4-(3-trifluoromethylstyryl)quinoline, 7.3 g (0.025 mole) of 4-bromo-1-phthalimidopentane and 2.5 g of triethylamine was heated in an oil bath at 130°–135° for 12 hr. The reaction mixture ws dissolved in chloroform and passed through a silica gel column to give 11 g of crude product which was used without further purification. Crystallization from ethanol provided an analytical sample as yellow needles, mp 154°–156°.

Anal. Calcd. for $C_{32}H_{28}F_3N_3O_3$: C, 68.68; H, 5.04; N, 7.51. Found: C, 68.49; H, 4.94; N, 7.38.

C.
8-(4-Amino-1-methylbutylamino)-6-methoxy-4-(3-trifluoromethylstyryl)quinoline Phosphate.

A mixture of 11 g of crude 6-methoxy-8-(1-methyl-4-phthalimidobutylamino)-4-(3-trifluoromethylstyryl)-quino line, 33 g of 95% hydrazine and 700 ml of ethanol was heated under reflux for 6 hr. The mixture was evaporated to dryness under reduced pressure and the residue was extracted with ether. The ether solution was extracted with dil HCl, the acid extract was basified with NH₄OH and the basic mixture was extracted with ether. The ether solution was treated with charcoal, dried (K₂CO₃) and evaporated. The residue (4.1 g) was dissolved in methanol and treated with methanolic H₃PO₄ to give the phosphate. Crystallization from methanol gave 2.3 g of yellow prisms, mp 216°–218°.

Anal. Calcd. for $C_{24}H_{26}F_3N_3O$: C, 54.64; H, 5.55; N, 7.97. Found: C, 54.27; H, 5.89; N, 8.00.

EXAMPLE 7.
8-(4-Amino-1-methylbutylamino)-2-ethyl-6-methoxyquinoline

A. 8-Amino-2-ethyl-6-methoxyquinoline.

A mixture of 75 g (0.344 mole) of 6-methoxy-8-nitroquinoline, 28.1 g (0.344 mole) of dimethylamine hydrochloride, 11.4 g of paraformaldehyde and 80 ml of ethanol was heated under reflux for 7 days. The cooled reaction mixture was diluted with ether and the solid collected by filtration. The crude product was recrystallized from ethanol. The yield of 2-(beta-dimethylaminoethyl)-6-methoxy-8-nitroquinoline hydrochloride (mp 195°–196°) was 71%.

Anal. Calcd. for $C_{14}H_{17}N_3O_3HCl\cdot\frac{1}{2}H_2O$: C, 52.42; H, 5.97; N, 13.10. Found: C, 52.45; H, 6.02; N, 13.13.

2-(beta-dimethylaminoethyl)-6-methoxy-8-nitroquinoline hydrochloride (76 g) was mixed with 800 ml of 1N NaOH and the solution extracted with ether. The ether extracts were washed with water, dried (Na₂SO₄), and concentrated. The residue was dissolved in 75 ml of ethanol, treated with 34.2 g of iodomethane and the mixture heated under reflux for ½ hr. The cooled reaction mixture was diluted with ether and the solid collected by filtration. The crude product was recrystallized from ethanol. There resulted 73.2 g (72% yield) of 6-methoxy-8-nitro-2-(beta-trimethylaminoethyl) quinoline iodide, mp 167°–168°.

Anal. Calcd. for $C_{15}H_{20}IN_3O_3$: C, 43.18; H, 4.83; N, 10.07; I, 30.42. Found: C, 43.37; H, 4.87; N, 10.09; I, 30.22.

A mixture of 73.2 g of 6-methoxy-8-nitro-2-(beta-trimethylaminoethyl)quinoline iodide, 1250 ml of 1N NaOH, and 1250 ml of chloroform was stirred mechanically at room temperature for 6 hr. The chloroform layer was separated, washed with water, dried (Na₂SO₄) and concentrated. 6-Methoxy-8-nitro-2-vinylquinoline (35.8 g) was obtained in 89% yield. A sample recrystallized from ethanol-chloroform melted at 156°–158°. $R_f$: 0.41 (benzene), 0.58 (chloroform), 0.59 (ethyl acetate); IR (KBr): 1630 and 1600 cm⁻¹ (C=C), 1510 cm⁻¹ (NO₂); NMR: (d—DMSO) δ 3.73 (s, 3H, OCH₃), 5.45 (q, 1H, HC=C—H), 6.1 (q, 1H, HC=CH),
           H                             H 6.6–7.0 (m, 1H), 7.35–8.20 (m, 4H).

To a mixture of 1.2 g of granular tin, 38.7 g of SnCl₂.2H₂O, 80 ml of conc HCl, and 40 ml of ethanol stirred and cooled to 0° was added 10 g of 6-methoxy-8-nitro-2-vinylquinoline portion-wise such that the temperature never exceeded 10°. After the addition was complete, the mixture was stirred at 10° for 1 hr, then at 25° for 2 hr. The mixture was cooled and basified with 40% NaOH solution. The solution was extracted with methylene chloride and the extracts were washed with water, dried (Na₂SO₄), and concentrated. The residual oil was eluted through a short silica gel column with methylene chloride to give 6.7 g (77%) of a yellow solid, this was 8-amino-6-methoxy-2-vinylquinoline. A sample recrystallized from hexane-ethanol melted at 120°–122°. $R_f$: 0.38 (benzene), 0.52 (chloroform), 0.59 (ethyl acetate).

Anal. Calcd. for $C_{12}H_{12}N_2O$: C, 71.98, H, 6.04; N, 13.99. Found: C, 71.88; H, 6.08; N, 13.92.

To a mixture of 9.6 g (0.04 mole) of 6-methoxy-8-nitro-2-vinylquinoline, 5 g (wet weight, washed with ethanol) of Raney nickel catalyst and 250 ml of toluene-95% ethanol (1:1) was added 25 ml of 85% hydrazine hydrate in portions, and after the vigorous reaction was over the mixture was heated under reflux for 5 hr. The condensor was removed and the mixture heated (ethanol added) until the vapors were faintly alkaline. The mixture was cooled, filtered over diatomaceous earth, and the filtrate concentrated in vacuo. The oily residue was dissolved in anhydrous ether and treated with HBr gas. The hydrobromide precipitated as a yellow powder and was recrystallized from ethanol-chloroform. The yield was 6.6 g (56%) of the desired 8-amino-2-ethyl-6-methoxyquinoline hydrobromide, mp 239°–241°. $R_f$: 0.62 (19.2 ethyl acetate-diethylamine), 0.67 (19:1 ethanol-diethylamine), 0.74 (19:1 methanol-diethylamine).

Anal. Calcd. for $C_{12}H_{14}N_2O\cdot HBr$: C, 50.90; H, 5.34; N, 9.89. Found: C, 50.91; H, 5.36; N, 9.88.

B.
8-(4-Amino-1-methylbutylamino)-2-ethyl-6-methoxyquinoline Maleate

A mixture of 15.2 g (0.075 mole) of 8-amino-2-ethyl-6-methoxyquinoline, 22.2 g (0.075 mole) of 2-bromo-5-phthalimidopentane, and 7.6 g (0.075 mole) of triethylamine was heated (oil bath temp. 135°) with stirring for 20 hrs. After 1 hr, 7.6 g of triethylamine was added; after 6 hr, 22.2 g of 2-bromo-5-phthalimidopentane and 7.6 g of triethylamine was added. The mixture was diluted with ether and the triethylamine hydrobromide was separated by filtration.

The ether filtrate was concentrated under vacuo and the residue was heated under reflux with 625 ml of 95% ethanol and 63 ml of 85% hydrazine hydrate for 3 hrs. The ethanol was removed under vacuo and the residual solid was stirred with 150 g of 50% KOH and methylene chloride for about ½ hour. The methylene chloride layer was evaporated and the aqueous layer was extracted with methylene chloride. The combined methylene chloride extract was washed with water, saturated NaCl solution and dried over anhydrous $Na_2SO_4$. The solvent was removed in vacuo, leaving the base, 8-(4-amino-1-methylbutylamino)-2-ethyl-6-methoxyquinoline.

The residue was dissolved in methanol, and treated with a solution of 12 g of maleic acid in methanol. Dilution with anhydrous ether caused separation of the maleate as an oil. The liquid was decanted, and the oil was dissolved in ethanol then diluted with anhydrous ether until turbidity occurred. On cooling, part of it separated as an oil, and the rest came out as solid material. This solid material (7.8 g, 26%) was again recrystallized from ethanol-ether; mp 111°–114°.

Anal. Calcd. for $C_{17}H_{25}N_3O.C_4H_4O_4$: C, 62.51; H, 7.24; N, 10.41. Found: C, 62.35; H, 7.25; N, 10.35.

EXAMPLE 8.
8-(4-Amino-1-methylbutyl)amino-6-methoxy-2-vinylquinoline Maleate.

A mixture of 12 g (0.06 mole) of 8-amino-6-methoxy-2-vinylquinoline (from Example 7A), 17.8 g (0.06 mole) of 2-bromo-5-phthalimidopentane, and 6.1 g (0.06 mole) of triethylamine was heated with stirring (oil bath temp. 130°) for 20 hrs. After 1 hr, 6.1 g of triethylamine was added; after 6 hrs., further amounts, 17.8 g of 2-bromo-5-phthalimidopentane and 6.1 g of triethylamine was added. The mixture was diluted with ether and the triethylamine hydrobromide was removed by filtration. The ether filtrate was concentrated under vacuo and the residue was heated under reflux with 500 ml of 95% ethanol and 50 ml of 85% hydrazine hydrate for 3 hrs. The ethanol was removed in vacuo, and the residual solid was stirred with 120 g of 50% KOH and ether. The ether layer was separated and the aqueous layer extracted with ether. The combined ether extracts were washed with water, saturated brine and dried over anhydrous $Na_2SO_4$. The solvent was removed in vacuo, then the residue was dissolved in methanol and treated with a solution of 9 g of maleic acid in methanol. Dilution with anhydrous ether caused separation of the salt as an oil. The liquid was decanted, and the oil was dissolved in ethanol. It was diluted with anhydrous ether until turbidity occurred. On cooling, most of it separated as an oil and 1.2 g of solid was obtained. Further attempts to crystallize the oil from ethanol-ether, ethyl acetate, chloroform, acetonitrile, and DMF-ether were unsuccessful. The solid material was twice recrystallized from ethanol-ether; mp 117°–120°. This was the desired maleate salt. Anal. Calcd. for $C_{17}H_{23}N_3O.C_4H_4O_4$: C, 62.83; H, 6.78; N, 10.47. Found: C, 62.62; H, 6.81; N, 10.40.

EXAMPLE 9.
8-(4-Amino-1-methylbutylamino)-4-ethyl-6-methoxyquinoline

A. 8-Amino-4-ethyl-6-methoxyquinoline.

4-Ethyl-6-methoxy-8-nitroquinoline was produced in 11% yield by carrying out a Skraup reaction on 4-methoxy-2-nitroaniline and ethyl vinyl ketone. It separated from methylene chloride-hexane as yellow crystals, mp 158.5°–159°.

The reduction of 4-ethyl-6-methoxy-8-nitroquinoline with tin and tin (II) chloride in alcoholic hydrochloric acid gave a dark oil, which was subjected to chromatography on activated alumina, and eluted with 25% tetrahydrofuran in benzene. There was obtained a 79% yield of yellow oil which solidified; mp 72°–74°. Following several crystallizations from methylene chloride-hexane, the 8-amino-4-ethyl-6-methoxyquinoline melted 74°–75°.

Catalytic reduction of the nitro compound with Raney nickel gave the same product, however the yield was only 60%.

B. 4-Ethyl-6-methoxy-8-(4-phthalimido-1-methylbutylamino)quinoline.

A mixture of 9.0 g of (0.045 mole) of 8-amino-4-ethyl-6-methoxyquinoline, 13.2 g (44.5 mmole) of 4-bromo-1-phthalimidopentane and 4 ml triethylamine was heated at 135° for 8 hr under a Dry Ice condenser. The reaction mixture was cooled, dissolved in methylene chloride, and filtered to remove triethylamine hydrobromide. The filtrate was concentrated to give a dark oil; the oil was dissolved in benzene and eluted through 500 g Florisil, using 2% THF/benzene as the eluent. An amber oil (14.56 g) resulted. This was chromatographed in 1.5 kg of alumina, using a gradient elution system of 2 l of 2% THF/benzene into 2 l benzene, finishing with 2% THF/benzene. The phthalimido compound resulted: 8.16 g (44%); ir ($CH_2Cl_2$) 3375 (N—H), 1745 and 1710 cm$^{-1}$ (imide C=O); nmr (CDCl$_3$) δ 1.31 (m, $CH_3CH_2$ and $CH_3CH$), 1.77 (m, CH$CH_2CH_2$CH$_2$N<), 2.97 (q, CH$_3CH_2$), 3.71 (t, $CH_2CH_2$N<), 3.88 (s, CH$_3$O), 6.28 and 6.43 (two d, 5 and 7H), 7.14 (d, 3H), 7.72 (m, phthaloyl), and 8.40 ppm (d, 2H).

This sample was used in the next experiment without further purification.

C. 8-(4-Amino-1-methylbutylamino)-4-ethyl-6-methoxyquinoline Dihydrobromide.

A solution of 8.16 g (0.0196 mole) of the foregoing phthalimido compound and 6 ml hydrazine hydrate in 200 ml ethanol was refluxed for 2 hr. The reaction mixture was cooled and the precipitated phthalhydrazide removed by filtration. The filtrate was concentrated and the residue dissolved in methylene chloride and filtered to remove last traces of the hydrazide. Concentration of the filtrate in vacuo gave 5.26 g (94%) of 8-(4-amino-1-methylbutylamino)-4-ethyl-6-methoxyquinoline; ir ($CH_2Cl_2$) 3375 cm$^{-1}$ (N-H), absence of C=O; nmr (CDCl$_3$) δ 1.24 (d, $CH_3$CH), 1.34 (t, CH$_3$CH$_2$) 1.64 (m, CHCH$_2$CH$_2$CH$_2$NH$_2$), 2.96 (q, CH$_3$CH$_2$), 3.88 (s, CH$_3$O), 4.10 (s, CH$_2$CH$_2$NH$_2$), 6.25 and 6.44 (two d, 5 and 7H), 7.12 (d, 3H), and 8.40 ppm (d, 2H). The dihydrobromide was prepared from the base in the standard manner. Recrystallization of the salt from ethanol-ether gave 8.08 g (98%), mp 214°–215°. The analytical sample prepared by recrystallization from the same solvent system had mp 216°–217°.

Anal. Calcd. for C$_{17}$H$_{25}$N$_3$O 2HBr: C, 45.45; H, 6.06; Br, 35.58; N, 9.35. Found: C, 45.50; H, 6.09; Br, 35.38; N, 9.11.

EXAMPLE 10.
8-(4-Amino-1-methylbutylamino)-2-(4-chlorobenzyloxy)-6-methoxyquinoline

A.
8-Amino-2-(4-chlorobenzyloxy)-6-methoxyquinoline.

6-Methoxy-8-nitroquinoline was converted into 2-chloro-6-methoxy-8-nitroquinoline: K. Mislow and J. B. Koepfli, J. Amer. Chem. Soc., 68, 1553 (1946); R. E. Lyle, et al., J. Org. Chem., 37, 3967 (1972).

A mixture of 48 g (0.2 mole) of 2-chloro-6-methoxy-8-nitroquinoline, 42.78 g (0.3 mole) of 4-chlorobenzyl alcohol, 27.6 g (0.2 mole) of anhydrous potassium carbonate, and 200 ml N,N-dimethyl formamide was heated under nitrogen at ca. 155°–160° for 18 hr. The mixture was cooled, diluted with ice water, stirred, collected, and washed with water. The crude solid was leached with a little 95% ethanol at 70° and then recrystallized from that solvent. A 84% yield of 2-(4-chlorobenzyloxy)-6-methoxy-8-nitroquinoline resulted; mp 129.5°–133.5°.

The foregoing nitro compound (34.48 g, 0.1 mole), 500 ml of a 1:1 mixture (v/v) of toluene and ethanol, 10 g wet Raney nickel, and 50 ml 85% hydrazine hydrate was refluxed for 6 hr. Thereafter, the condenser was placed for distillation and heated until vapors at the still-head were alkaline. A small amount of hydroquinone was added, and the hot mixture filtered. The filtrates were concentrated in vacuo, leached with a little warm ethanol, then crystallized from ethanol (charcoal). The 8-amino-2-(4-chlorobenzyloxy)-6-methoxyquinoline was obtained in 97% yield; mp 123.5°–125°.

B.
2-(4-Chlorobenzyloxy)-6-methoxy-8-(4-phthalimido-1-methylbutylamino)quinoline.

A mixture of 6.3 g (0.02 mole) 2-(4-chlorobenzyloxy)-6-methoxy-8-aminoquinoline, 6.0 g (0.02 mole) 2-bromo-5-phthalimidopentane, and 2.0 g (0.02 mole) triethylamine was heated at 135° for 14 hr. After 1.4 hr., 2.0 g triethylamine was added; after 4.25 hr. 6.0 g of bromophthalimidopentane was added; and after 5.25 hr. 2.0 g triethylamine was added to the reaction mixture. The reaction mixture was extracted with 200 ml anhydrous ether and the sticky hydrobromide washed with 50 ml benzene. The yield of triethylamine hydrobromide was quantitative. The solvents were removed in vacuo and the oil allowed to stand for two weeks, whereupon it became crystalline. The semi-solid was washed with ethanol, then stirred with 40 ml ether-petroleum ether (1:1). The solvents were decanted and the solid stirred with a fresh portion, filtered, and washed with the solvent. There was obtained 6.0 g, mp 90°–93°. The combined filtrates were cooled and 1.35 g, mp 90°–93°, was obtained. After purification a sample melted at 94.5°–96°. The yield of phthalimido derivative was 69%, based on starting amine. (The sodium acetate buffer method gave only 25% yield.)

C.
2-(4-Chlorobenzyloxy)-6-methoxy-8-(4-amino-1-methylbutylamino)-quinoline Maleate.

A mixture of 7.5 g (0.014 mole) 2-(4-chlorobenzyloxy)-6-methoxy-8-(4-phthalimido-1-methylbutylamino)-quinoline (crude), 6.0 ml 85% hydrazine hydrate, and 100 ml 95% ethanol was refluxed 3 hr. After standing overnight, the mixture was stirred with ether and 20 g 50% aq. KOH. The ether layer was washed with water and sat'd. brine. The aqueous portions were extracted with ether and the washing process repeated. A sat'd solution of 2.0 g maleic acid in methanol was added to the dried (MgSO$_4$) ether solution. There was obtained 5.10 g (71%) of an off-white solid, mp 173°–177°. Recrystallization of the crude maleate from 120 ml 95% ethanol (charcoal) afforded 3.55 g, mp 174°–178°. Further recrystallization from ethanol gave the analytical sample, mp 176°–177.5°.

Anal. Calcd. for C$_{22}$H$_{26}$ClN$_3$O$_2$·C$_4$H$_4$O$_2$: C, 60.52; H, 5.86; N, 8.14; Cl, 6.87. Found: C, 60.46; H, 55.92; N, 8.12; Cl, 6.92.

EXAMPLE 11.
2-Amino-8-(4-amino-1-methylbutylamino)-6-methoxyquinoline

A. 2-Acetamido-8-amino-6-methoxyquinoline.

A mixture of 50.4 g (0.21 mole) of 2-chloro-6-methoxy-8-nitroquinoline (cf. Example 10A) and 490 g of phenol was heated at 170°–180° under ammonia atmosphere for 1½ hr. The mixture was cooled and treated with 50% NaOH solution. The yellow precipitate was collected and dried (34.8 g). The crude product was a mixture of 2-amino-6-methoxy-8-nitroquinoline and 6-methoxy-8-nitro-2-phenoxyquinoline. That mixture was treated with hot 30% acetic acid and filtered. The filtrate was basified with sodium hydroxide solution and the yellow precipitate was collected and dried to give 26.8 g (58%) of 2-amino-6-methoxy-8-nitroquinoline. The analytical sample was obtained by sublimation: mp 195°–197°.

Anal. Calcd. for C$_{10}$H$_9$N$_3$O$_3$: C, 54.79; H, 4.14; N, 19.17. Found: C, 54.71; H, 4.17; N, 19.26.

A mixture of 10 g of 2-amino-6-methoxy-8-nitroquinoline and 70 ml of acetic anhydride was heated under reflux for 3 hr. The excess acetic anhydride was removed in vacuo, the solid was collected, washed with water and dried (10.7 g, 90%). The crude 2-acetamido-6-methoxy-8-nitroquinoline (mp 298°–301°) was reduced to the 8-amino derivative without further purification.

A mixture of 10.5 g (0.04 mole) of crude 2-acetamido-6-methoxy-8-nitroquinoline, 14 g of iron filings, 2 ml of glacial acetic acid, and 120 ml of water was stirred on the steam bath for 18 hr. The mixture was filtered and the solid residue was washed thoroughly with acetone. The acetone washings were concentrated and the residue was eluted through a short silica gel column with methylene chloride to give 7.3 g (78%) of 2-acetamido-8-amino-6-methoxyquinoline. A sample recrystallized from 95% ethanol melted at 192°–194°.

Anal. Calcd for C$_{12}$H$_{13}$N$_3$O$_2$: C, 62.33; H, 5.67; N, 18.17. Found: C, 62.37; H, 5.69; N, 18.12.

B.
2-Amino-8-(4-amino-1-methylbutylamino)-6-methoxyquinoline Maleate.

A mixture of 11.6 g (0.05 mole) of 2-acetamido-8-amino-6-methoxyquinoline, 14.8 g (0.05 mole) of 2-bromo-5-phthalimidopentane, and 5.1 g (0.05 mole) of triethylamine was heated (oil bath temp. 135°) with stirring for 20 hrs. After 1 hr, 5.1 g of triethylamine was added; after 6 hr, 14.8 g of 2-bromo-5-phthalimidopentane and 5.1 g of triethylamine were added. The mixture was diluted with ether and the triethylamine hydrobromide was separated by filtration. The ether filtrate was concentrated under vacuo and the residue was heated under reflux with 400 ml of 95% ethanol and 40 ml of 85% hydrazine hydrate for 3 hrs. The mixture was stirred and heated under reflux with 120 g of 50% KOH for 2 hrs. The ethanol was removed in vacuo and the residue was extracted with methylene chloride. The methylene chloride extracts were washed with water, saturated brine and dried over anhydrous $Na_2SO_4$. The solvent was removed in vacuo, the residue was dissolved in ether-methanol and treated with a solution of 12 g of maleic acid in methanol. The salt separated as a powder and was recrystallized from methanol. The first crop was found to be 2,8-diamino-6-methoxy-quinoline maleate (5.7 g): mp 203°–205°; $R_f$: 0.46 (19:1 ethyl acetate-diethylamine), 0.50 (19:1 ethanol-diethylamine), 0.58 (19:1 methanol-diethylamine).

Anal. Calcd. for $C_{10}H_{11}N_3O.C_4H_4O_4$: C, 55.08; H, 4.95; N, 13.76. Found: C, 55.02; H, 5.21; N, 13.57.

The methanol mother liquor after concentration and cooling gave 4.3 of 2-amino-8-(4-amino-1-methylbutylamino)-6-methoxyquinoline maleate. This was twice recrystallized from methanol: mp 168°–170°; $R_f$: 0.19 (19:1 ethylacetatediethylamine), 0.39 (19:1 ethanol-diethylamino), 0.50 (19:1 methanol-diethylamine).

Anal. Calcd. $C_{15}H_{22}N_4O.2C_4H_4O_4$: C, 54.54; H, 5.97; N, 11.06. Found: C, 54.68; H, 6.00; N, 11.13.

EXAMPLE 12.
8-(4-Amino-1-methylbutylamino)-6-methoxy-1-methyl-1,2,3,4-tetrahydroquinoline

A.
8-Amino-6-methoxy-1-methyl-1,2,3,4-tetrahydroquinoline.

6-Methoxy-8-nitroquinoline was converted into its methiodide (mp 155°–157°) in 90–95% yield after the method of K. Mislow and J. B. Koepfli [J. Amer. Chem. Soc., 68, 1153 (1946)].

Reduction of the methiodide in aqueous solution was done with sodium borohydride. A 97% yield of dark red crystals of 6-methoxy-1-methyl-8-nitro-1,2-dihydroquinoline resulted. Recrystallization from a mixture of ether and hexane gave the pure compound which melted 56°–61°, resolidified and melted again at 174°–180°.

Anal. Calcd. for $C_{11}H_{12}N_2O_3$: C, 59.99; H, 5.49; N, 12.72. Found: C, 59.68; H, 5.28; N, 12.87.

The foregoing nitro compound was dissolved in ethanol and reduced catalytically in the presence of Raney nickel. Crude 8-amino-6-methoxy-1-methyl-1,2,3,4-tetrahydroquinoline was isolated from the filtered liquors. This residue afforded a 69% yield of compound melting 74°–75° when crystallized from a mixture of methylene chloride and hexane.

Anal. Calcd. for $C_{11}H_{14}N_2O$: C, 68.71; H, 8.39; N, 14.57. Found: C, 68.48; H, 8.40; N, 14.71.

B.
8-(4-Amino-1-methylbutylamino)-6-methoxy-1-methyl-1,2,3,4-tetrahydroquinoline Fumarate.

A mixture of 5.0 g (26.0 mmol) of 8-amino-6-methoxy-1-methyl-1,2,3,4-tetrahydroquinoline, 7.22 g (26.0 mmol) of 2-bromo-5-phthalimidopentane, and 3 ml of triethylamine was heated at 135° (under a Dry Ice condenser) for 8 hr. The reaction mixture was cooled, dissolved in acetone, and filtered to remove triethylamine hydrobromide. The filtrate was concentrated to give 11.26 g of a dark oil. Chromatography on alumina, eluting with benzene, afforded 1.65 g (16%) of 6-methoxy-1-methyl-8-(4-phthalimido-1-methyl-butylamino)-1,2,3,4-tetrahydroquinoline as a yellow oil: ir ($CH_2Cl_2$) 1710 cm$^{-1}$ (amide C=O); nmr ($CDCl_3$) & 1.18 (d, $CH_3CH$), 1.70 (m, methylene protons of ring), 2.54 (s, $NCH_3$), 2.70 [t, $CH_2$—N—(pht)], 3.00 (t, $CHCH_2CH_2$), 3.69 (s, $OCH_3$), 6.42 (m, $CH_3CHCH_2$), 5.85 and 5.96 (2 d, 5, 7H), 7.72 ppm (m, phthaloyl protons).

The intermediate was treated with hydrazine hydrate in ethanol to produce an 89% yield of the base as a yellow oil. A 93% conversion into the fumarate salt resulted; mp 169°–171°. It melted 170°–172° following recrystallization from ethanol-ether: nmr (polysol) & 1.18 (d, $CH_3CH$), 1.70 (m, methylene protons of ring), 2.50 (s, $NCH_3$), 2.65 (t, $CH_2NH_2$), 2.95 (t, $CHCH_2CH_2$), 3.64 (s, $OCH_3$), 5.81 and 5.89 (2 d, 5 7H), 6.44 (s, CH=CH).

Anal. Calcd. for $C_{16}H_{26}N_3O.\frac{3}{2}C_4H_4O_4$: C, 64.45; H, 8.71; N, 12.53. Found: C, 64.11; H, 8.75; N, 12.68.

EXAMPLE 13.
8-(4-Amino-1-methylbutylamino)-5-(4-chlorobenzyloxy)-6-methoxyquinoline.

A. 5-(4-Chlorobenzyloxy)-6-methoxy-8-nitroquinoline.

6-Methoxy-8-nitroquinoline was converted into 5-bromo-6-methoxy-8-nitroquinoline according to Elderfield, et al [J. Org. Chem., 23, 1378 (1958)]. By treatment of the 5-bromo compound with aqueous methanolic potassium hydroxide, the orange-colored potassium salt of 5-hydroxy-6-methoxy-8-nitroquinoline was prepared [cf. R.C. Fuson, et al., J. Org. Chem., 11, 799 (1947)].

A mixture of 28.4 g (0.11 mole) of the above potassium salt, 19.3 g (0.12 mole) of 4-chlorobenzyl chloride and 300 ml of N,N-dimethylformamide (DMF) was stirred and heated at 90° under nitrogen atmosphere for 25 hrs. Most of the DMF was removed on a rotary evaporator, the residue was poured into cold water and stirred for 15 min. The solid was collected and dried to give 30.8 g (81%) of crude 5-(4-chlorobenzyloxy)-6-methoxy-8-nitroquinoline. The analytical sample was obtained by twice recrystallizing from 1:1 ether-petroleum ether; mp 115°–116°.

Anal. Calcd. for $C_{17}H_{13}ClN_2O_4$: C, 59.23; H, 3.80; N, 8.13; Cl, 10.28. Found: C, 59.44; H, 3.91; N, 8.09; Cl, 10.14.

B.
8-Amino-5-(4-chlorobenzyloxy)-6-methoxyquinoline.

The foregoing 8-nitro compound was reduced with iron filings in aqueous acetic acid at 80°. The crude product was recrystallized from 1:1 ether and petroleum ether to give a 75% yield of 8-amino-5-(4-chlorobenzyloxy)6-methoxyquinoline, mp 121.5°–123°.

Anal. Calcd. for $C_{17}H_{15}ClN_2O_2$: C, 64.87; H, 4.80; N, 8.90; C, 11.26. Found: C, 65.01; H, 4.85; N, 8.89; Cl, 11.17.

C.
8-(4-Amino-1-methylbutylamino)-5-(4-chlorobenzyloxy)-6-methoxy-quinoline.

A mixture of 4.72 g (0.015 mole) of intermediate from B, above, 4.5 g (0.015 mole) of 2-bromo-5-phthalimidopentane, and 1.52 g (0.015 mole) of triethylamine was heated at 100° for 74 hrs. After 2 hrs, 1.52 g of triethylamine was added and after 8 hrs, 4.5 g of 2-bromo-5-phthalimidopentane and 1.52 g of triethylamine were added. The mixture was diluted with ether and filtered to remove the triethylamine hydrobromide. The solvents were concentrated and the oil (6.7 g) refluxed with 12 ml (excess) of 85% hydrazine hydrate and 130 ml of 95% ethanol for 3 hrs. A voluminous solid separated, ethanol was removed under reduced pressure, and the semisolid mixture was stirred with 30 g of 50% aq. KOH and 150 ml of ether for 15 min. The ether layer was separated, washed with water and saturated brine. The aqueous layer was extracted with ether and the washings repeated. The combined ether solutions were dried ($Na_2SO_4$) and concentrated. The oil (2.6 g) was redissolved in anhydrous ether and treated with a saturated solution of 1.3 g of maleic acid in methanol. Dilution with ether and cooling gave the dimaleate. It had mp 138°–140.5°. $R_f$: 0.31 (19.1 ethyl acetate-diethylamine), 0.42 (19:1 chloroform-diethylamine), 0.53 (19:1 methanol-diethylamine); nmr ($CDCl_3$) & 8.75–6.70 (m, 14H), 6.19 (s, 4H), 5.00 (s, 2H), 4.01 (s, 3H), 3.10–2.41 (m, 3H), 2.00–1.50 (m, 4H), 1.27 (d, 3H). Analyses of this salt were vitiated by presence of a small amount of inorganic material. Accordingly, the base was liberated from the dimaleate for analysis.

Anal. Calcd. for $C_{22}H_{26}Cl_{N3}O_2$: C, 66.07; H, 6.55; Cl, 8.86; N, 10.51. Found: C, 66.39; H, 5.80; Cl, 9.18; N, 10.48.

EXAMPLE 14.
8-(4-Amino-1-methylbutylamino)-5-(4-chlorophenoxy)-6-methoxy-quinoline.

A. 8-Amino-5-chlorophenoxy)-6-methoxyquinoline.

The potassium salt of p-chlorophenol was prepared by powdering 4-chlorophenol (20 g, 0.16 mole) and KOH pellets (86%, 12 g) in a mortar under nitrogen in a polyethylene bag. The mixture in EtOH (200 ml) was heated at reflux for 2 hr. Removal of the solvent in vacuo provided anhydrous potassium 4-chlorophenolate. The latter, 5-bromo-6-methoxy-8-nitroquinoline (cf. Example 13, A) (20 g. 0.07 mole) and doxane (400 ml) were then heated under reflux for 2 hr. The reaction mixture was cooled, diluted with ether (600 ml) and filtered. After removal of the solvent in vacuo and trituration of the residue with MeOH, 5-(4-chlorophenoxy)-6-methoxy-8nitroquinoline was obrtained as pale yellow, solid, mp 178°–179°. A further crystallization from ethanol raised the melting point to 180°–181°.

The foregoing nitroquinoline was reduced with iron in aqueous acetic acid. There resulted an 89% yield of 8-amino-5-(4-chlorophenoxy)-6-methoxyquinoline, which crystallized well from methanol. It melted 117°–118°.

Anal. Calcd. for $C_{16}H_{13}ClNO_2$: C, 63.89; H, 4.35; N, 9.31. Found: C, 63.70; H, 4.30; N, 9.21.

B.
5-(4-Chlorophenoxy)-6-methoxy-8-(4-phthalimido-1-methylbutylamino)-quinoline.

A stirred mixture of 8-amino-5-(4-chlorophenoxy)-6-methoxyquinoline (6.2 g, 0.02 mole), 4-bromo-1-phthalimidopentane (6.0 g, 0.02 mole), and triethylamine (2.0 g, 0.02 mole) was heated at 130°–135° for 12 hr. The cooled mixture was extractively treated with arm acetone (50 ml), cooled, and triethylamine hydrobromide collected (3.2 g, 89%). The filtrates were concentrated to dryness, and the residues taken up in chloroform, then treated with 48% hydrobromic acid. The chloroform layer was dried and concentrated, then absolute ether added to precipitate the hydrobromide of the desired compound (8.2 g, 70% yield). As obtained, the hydrobromide melted 194°–198°; following crystallization from ethanol, mp 214°–215°. It analyzed as a monohydrate. The base was liberated as a crystalline solid of mp 75°–77°.

Anal. Calcd. for $C_{29}H_{26}ClN_3O_4.HBr.H_2O$: C, 56.64; H, 4.76; N, 6.83. Found: C, 56.76; H, 4.66; N, 6.26.

C.
8-(4-Amino-1-methylbutylamino)-5-(4-chlorophenoxy)-6-methoxyquinoline.

Treatment of the base from Example 14B with hydrazine in ethanol was done in the usual manner. The desired base was isolated in 58% yield as a monohydrate, mp 82°–85°. Attempts to prepare salts give hygroscopic material not as stable as was the hydrated base.

Anal. Calcd. for $C_{21}H_{24}ClN_3O_2.H_2O$: C, 62.44; H, 6.48; N, 10.40. Found: C, 62.28; H, 6.27 N, 10.27.

EXAMPLE 15.
8-(4-Amino-1-methylbutylamino)-5-ethoxy-6-methoxyquinoline.

A. 8-Amino-5-ethoxy-5-ethoxy-6-methoxyquinoline.

5-Bromo-6-methoxy-8-nitroquinoline was made according to Example 13A. It was converted into 5,6-dimethoxy-8-nitroquinoline in 70% yield by reaction with sodium methoxide in methanol containing pyridine. It separated from methanol as yellowish crystals, mp 125°–128°.

5,6-Dimethoxy-8-nitroquinoline (20 g, 0.08 mole) was boiled for 6 hr in a mixture of 10 ml conc. HCl and 200 ml of water. A reddish precipitate resulted; that was treated with 500 ml of 1% NaOH, filtered, and acidified. The orange solid (17.0 g, 90% yield) was 5-hydroxy-6-methoxy-8-nitroquinoline; mp 243°–245° dec.

The action of $POCl_3$ served to convert the foregoing quinoline derivative into 5-chloro-6-methoxy-8-nitroquinoline in 97% yield. The product melted 204°–206°.

5-Ethoxy-6-methoxy-8-nitroquinoline resulted in 80% yield by the action of refluxing ethanolic KOH solution on the 5-Cl intermediate. It separated from ligroin as yellow crystals, mp 98°–99.5°.

Anal. Calcd. for $C_{12}H_{12}N_2O_4$: C, 58.06; H, 4.87; N, 11.20. Found: C, 57.87; H, 4.68; N, 11.11.

8 Amino-5-ethoxy-6-methoxyquinoline was obtained in 71% yield by catalytic reduction of the nitro compound using Adams' platform. The compound crystallized well from ligroin; mp 132.5°–133.5°.

Anal. Calcd. for $C_{12}H_{14}N_2O_2$: C, 66.03; H, 6.47; N, 12.84. Found: C, 66.28; H, 6.31; N, 12.64.

B.
5-Ethoxy-6-methoxy-8-(1-methyl-4-phthalimidobutylamino)quinoline.

A stirred mixture of 8-amino-5-ethoxy-6-methoxyquinoline (8.4 g, 0.0884 mole) and 4-bromo-1-phthalimidopentane (14.4 g, 0.048 mole) was treated at 150°-155° while triethylamine (5.6 g, 0.056 mole) was added in portions during 2 hr. The very dark mixture was continued at 150° for 4 hr and allowed to cool overnight. It was re-heated to 150°, treated with more 4-bromo-1-phthalimidopentane (14.4 g), in a single portion, and with triethylamine (5.6 g), portionwise during 2 hr, and then allowed to stir at 150° for 2 additional hr. The latter addition sequence was repeated three more times, the mixture was allowed to cool, diluted with acetone (300 ml) and filtered to yield (after washing with Me$_2$CO) 30.2 g (99%) of triethylamine hydrobromide. The filtrate was concentrated under vacuum and the residual mush was triturated with 400 ml of warm ether. A dark brown solid (2.7 g) was filtered (discarded) and the filtrate was dried (Drierite) and twice treated with carbon. The orange-brown solution was treated with excess ethereal HCl and the resulting red-orange precipitate was allowed to coagulate and then washed repeatedly with ether. The tacky-red-brown solid was basified with 10% NH$_4$OH and the yellow mixture was extracted with chloroform (2×300 ml). The combined extracts were dried (Drierite), treated with carbon and taken to dryness in vacuo. The remaining brown-orange gum (13.5 g, 77%) was used in the next step without further purification. Tlc of this material (silica, CHCl$_3$, I$_2$ visualization) revealed a single spot.

C.
8-(4-Amino-1-methylbutylamino)-5-ethoxy-6-methoxyquinoline Fumarate.

An orange-brown solution of 13.6 g (0.031 mole) of the foregoing phthalimido compound, 657 ml of ethanol, 398 ml of chloroform and 20 ml of 95% hydrazine was heated under reflux for 6 hr, allowed to cool overnight, and filtered to remove 4.9 g (after washing with ethanol and chloroform) of phthalhydrazide (97% of theory). The orange-brown filtrate was evaporated in vacuo and the residual mush was treated with 800 ml of ether. The mixture was extracted with 30% KOH (2×250 ml), water (3×100 ml), dried (Drierite, treated with carbon and filtered. The yellow filtrate was concentrated, under reduced pressure, to 500 ml and the stirred concentrate was treated, portionwise, with a hot solution of 3.65 g (0.031 mole) of fumaric acid in 100 ml of 2-propanol. The thick yellow precipitate was filtered, washed with cold 2-propanol and ether and vacuum-dried to give 7.9 g (60%) of product as an orange solid, mp 155°-157°. Crystallization from 2-propanol (carbon) provided 6.3 g of golden yellow solid, mp 154°-156°.

Anal. Calcd. for $C_{17}H_{25}N_3O_2 \cdot C_4H_4O_4$: C, 60.13; H, 6.97; N, 10.02. Found: C, 60.25; H, 6.97; N, 9.82.

EXAMPLE 16.
8-(4-Amino-1-methylbutylamino)-5-dimethylamino-6-methoxy-quinoline A. 8-Amino-5-dimethylamino-6-methoxyquinoline.

A solution of 18 g (0.22 mole) of dimethylamine hydrochloride in 50 ml of warm water was added to a stirred mixture of 30 g (0.11 mole) of 5-bromo-6-methoxy-8-nitroquinoline—Example 13A—30 g of NaHCO$_3$ and 180 ml of pyridine. The mixture was heated under reflux for 30 hr, allowed to cool and filtered. The filtered solid was washed with acetone and the combined filtrate and washings were slowly diluted with water to 4 l. Unreacted 5-bromo compound separated first followed by product. Crystallization from methanol gave 4.9 g of 5-dimethylamino-6-methoxy-8-nitroquinoline (20% yield) as orange crystals which melted 79°-80°.

The foregoing 8-nitro compound was reduced in aqueous acetic acid by addition of iron filings. 8-Amino-5-dimethylamino-6-methoxyquinoline was isolated as a dark oil, which could be distilled at ca. 100° at 0.1 mm. The distillate solidified to a yellow mass, which was crystallized from ether (95% yield of yellow needles, mp 105°-108°), and then washed with petroleum ether. The product then melted 109°-111°.

Anal. Calcd. for $C_{12}H_{15}N_3O$: C, 66.33; H, 6.96; N, 19.35. Found: C, 66.55; H, 6.72; N, 19.23.

B.
5-Dimethylamino-6-methoxy-8-(1-methyl-4-phthalimidobutylamino)-quinoline.

A stirred mixture of 17.2 g (0.033 mole) of 8-amino-5-dimethylamino-6-methoxyquinoline and 9.8 g (0.033 mole) of 4-bromo-1-phthalimidopentane was maintained at 145° while 5 ml of triethylamine was added dropwise. Addition of 9.8 g of 4-bromo-1-phthalimidopentane and 5 ml of triethylamine was repeated three more times, at the same temperature (145°) at 2 hr intervals. The mixture was allowed to cool, diluted with acetone and filtered. The filtrate was concentrated to a brown oil which was diluted with ether, washed with 30% KOH and extracted with chloroform. The extract was passed through a silica column and the eluate was concentrated, dissolved in ether, treated with Darco and slowly evaporated to give yellow crystals which, after washing with petroleum ether (bp 20°-40°) weighed 9.5 g and melted at 103°-105°.

Anal. Calcd. for $C_{25}H_{28}N_4O_3$: C, 69.42; H, 6.53; N, 12.96. Found: C, 69.29; H, 6.63; N, 12.76.

C.
8-(4-Amino-1-methylbutylamino)-5-dimethylamino-6-methoxyquinoline.

A mixture of 8.2 g (0.019 mole) of the intermediate phthalimido compound, 50 ml of chloroform, 550 ml of ethanol and 20 ml of 95% hydrazine was heated under reflux for 3.5 hr, allowed to cool and filtered. The filtrate was concentrated to a pale orange syrup, diluted with ether, washed with 30% KOH and extracted with 20% HCl. The extract was washed with ether, basified with 30% KOH and extracted with ether. The extract was dried (K$_2$CO$_3$) concentrated and distilled to give 5.3 g (93%) of free base, bp 156°-166°/0.1 mm. A further distillation of the base (bp 150°/0.06 mm) was done to obtain the analytical sample.

Anal. Calcd. for $C_{17}H_{26}N_4O$: C, 67.50; H, 8.67; N, 18.53. Found: C, 67.27; H, 8.78; N, 18.35.

5 g of base was dissolved in 100 ml of ethanol and treated with 64 ml of 5% ethanolic citric acid. The pale orange solution was diluted with 100 ml of ether and allowed to stand at room temperature overnight to give 7.8 g (96% on base) of the desired citrate after drying at 50°-55° and 0.07 mm. Crystallization from ethanol gave the analytical sample as yellow crystals with an indefinite melting point starting at about 100°.

Anal. Calcd. for $C_{17}H_{26}N_4O \cdot C_6H_8O_7$: C, 55.86; H, 6.93; N, 11.33. Found: C, 56.12; H, 7.16; N, 11.09.

EXAMPLE 17.
8-(4-Amino-1-methylbutylamino)-5,6-dimethoxy-4-methylquinoline

A. 8-Amino-5,6-dimethoxy-4-methylquinoline.

A Skraup reaction of 4,5-dimethoxy-2-nitroaniline with methyl vinyl ketone gave a 27% yield of 5,6-dimethoxy-4-methyl-8-nitroquinoline. The yellow compound crystallized well from methanol; mp 126°–127.5°.

The nitro compound was reduced catalytically in ethanol-dioxane with use of Raney nickel. An 84% yield of 8-amino-5,6-dimethoxy-4-methylquinoline resulted. It could be crystallized from cyclohexane or from benzene-petroleum ether mixture; mp 108°–110° (softening at 103°).

B.
8-(4-Amino-1-methylbutylamino)-5,6-dimethoxy-4-methylquinoline Diphosphate.

A stirred mixture of 4-methyl-5,6-dimethoxy-8-aminoquinoline (3.8 g, 0.017 mole), 4-iodo-1-phthalimidopentane (5.95 g, 0.017 mole) and triethylamine (1.7 g, 0.017 mole) was heated at 145° for 30 min. The mixture was then treated with an additional equivalent of 4-iodo-1-phthalimidopentane (5.95 g) and triethylamine (1.7 g) and maintained at 145° for 3 hr. The mixture was extracted with chloroform, washed with water, dried ($K_2CO_3$) and the solvent was evaporated. The residue was dissolved in ether and treated with ether-HCl. The red-orange solid which separated was collected, dissolved in water, treated with $NH_4OH$ and extracted with chloroform. The extract was dried ($K_2CO_3$) and concentrated under reduced pressure. The crude phthalimido intermediate (5.5 g) was dissolved in ethanol (50 ml) containing 75% hydrazine hydrate (5 ml) and refluxed for 5 hr. The mixture was concentrated to dryness and the residue was shaken with hot chloroform and phthalyl hydrazide was separated. The chloroform solution was washed with water, dried ($K_2CO_3$), treated with Norit and concentrated. The residue was dissolved in ether (ca. 200 ml) and treated with excess 1 M $H_3PO_4$ in ethanol. The solid was separated and recrystallized from ethanol to give 5.8 g (67%) of the target compound, mp 100°–104°.

Anal. Calcd. for $C_{17}H_{25}N_3O_2 \cdot 2H_3PO_4 \cdot \frac{1}{2}H_2O$: C, 40.16; H, 6.34; N, 8.27; P, 12.18. Found: C, 40.31; H, 6.39; N, 8.42; P, 12.34.

EXAMPLE 18.
8-(4-Amino-1-ethylbutylamino)-5,6-dimethoxy-4-methylquinoline

A.
5,6-Dimethoxy-4-methyl-8-(4-phthalimido-1-ethylbutylamino) quinoline.

A solution of 4-methyl-5,6-dimethoxy-8-aminoquinoline (0.042 mole) in 2-ethoxyethanol (21 ml) containing triethylamine (5.8 ml) and 1-phthalimido-4-iodohexane (14.9 g, 0.042 mole) was heated at 110° for 2.5 hr. Thereafter, there were two incremental additions of triethylamine and side-chain over 6 hrs, and the heating at 110° continued overnight. Th reaction mixture was diluted with chloroform and washed with water (×2). The organic layer was dried ($K_2CO_3$) and the solvents were removed in vacuo. The residue was dissolved in ether, filtered and acidified with excess ethereal HCl. The red gum which separated was crystallized from ethanol (150 ml) to yield 5,6-dimethoxy-4-methyl-8-(4-phthalimido-1-ethylbutylamino)quinoline hydrochloride (13 g, 63%), mp 163°–166°.

Anal. Calcd. for $C_{26}H_{29}N_3O_4 \cdot HCl \cdot 0.5\ H_2O$ (493.0): C, 63.34; H, 6.34; N, 8.52. Found: C, 63.30; H, 6.57; N, 8.48.

B.
8-(4-Amino-1-ethylbutylamino)-5,6-dimethoxy-4-methylquinoline Hemisuccinate.

The above phthalimide (12.2 g, 0.025 mole) was converted to the base by shaking with dilute $NH_4OH$ and methylene chloride. The organic layer was concentrated in vacuo. The oily residue was heated at reflux for 3 hr in ethanol (300 ml) containing 75% hydrazine hydrate (4.9 ml). After cooling, the solid (phthalyl hydrazide) was filtered and the filtrate was concentrated. The residue was shaken with 10% aqueous KOH and methylene chloride. The organic layer was dried ($K_2CO_3$) and concentrated. The oil was dissolved in petroleum ether (bp 30°–60°), treated with charcoal, filtered and concentrated. The base (7 g) was dissolved in methanol (100 ml) and succinic acid (1.4 g, 0.54 molar equivalent) was added with stirring. The methanol was removed under reduced pressure and the yellow foam was boiled in acetonitrile (100 ml). The solid was filtered and recrystallized from acetonitrile and ethanol (9:1, 150 ml) to yield 8-(4-amino-1-ethylbutylamino)-5,6-dimethoxy-4-methylquinoline hemisuccinate (6 g, 64%), mp 136°–137°.

Anal. Calcd. for $C_{18}H_{27}N_3O_2 \cdot 0.5\ C_4H_6O_4$: C, 63.80; H, 8.03; N, 11.16. Found: C, 63.55; H, 8.01; N, 11.41.

EXAMPLE 19.
8-(4-Aminopentylamino)-5,6-dimethoxy-2,4-dimethylquinoline

A. 8-Amino-5,6-dimethoxy-2,4-dimethylquinoline.

4,5-Dimethoxy-2-nitroaniline and 3-penten-2-one were subjected to a Skraup reaction. A black, tarry substance was obtained, from which an orange solid could be isolated by chromatography over silica gel using benzene-ethyl acetate (19:1) to elute the product. That material was thrice crystallized from 2-propanol, re-chromatographed, and again crystallized to afford 14% yield of golden 5,6-dimethoxy-2,4-dimethyl-8-nitroquinoline. Although it melted 85°–108°, it showed a single spot on two tlc systems.

The foregoing nitro compound was reduced after the procedure used for 4-methyl analogue (Example 17A). A 90% yield of desired product resulted as a cream-colored solid; mp 107.5–109.5°.

B.
5,6-Dimethoxy-2,4-dimethyl-8-(4-phthalimidopentylamino) quinoline.

A solution of 8-amino-5,6-dimethoxy-2,4-dimethylquinoline (20.0 g, 86 mmole), 1-iodo-4-phthalimidopentane (38.4 g, 112 mmole) and triethylamine (11.3 g, 112 mmole) in 2-ethoxyethanol (230 ml) was heated at reflux (135° C.) for 5 hr. After cooling, the solution was diluted with 5% aqueous sodium bicarbonate (0.5 l) and then extracted with methylene chloride (2×250 ml). The combined extracts were washed with water (2×250 ml) and brine (100 ml) and then dried (potassium carbonate). Filtration, then evaporation of the solvents, afforded a black tar. The tar was chromatographed over silica gel (0.7 kg) with benzene. The orange-brown material eluting first from the column was crystallized from ethanol (10% solution), affording 12.7 g (33%) of the title compound as orange plates, mp 141°–144°. Further recrystallization of a small amount gave an analytical sample with mp 144.5°–146.5°; the analysis was satisfactory after drying at 110° (the analysis corresponded to a hemihydrate after drying at 78°).

Anal. Calcd. for $C_{26}H_{29}N_3O_4$: C, 69.78; H, 6.53; N, 9.39. Found: C, 70.09; H, 6.82; N, 9.62.

C.
8-[(4-Aminopentyl)amino]-5,6-dimethoxy-2,4-dimethylquinoline Phosphate.

A solution of 5,6-dimethoxy-2,4-dimethyl-8-[(4-phthalimidopentyl)-amino]quinoline (12.7 g, 28 mmole) in ethanol (270 ml) containing 75% hydrazine (5.6 g, 84 mmole) was refluxed for 18 hr. An additional portion of 75% hydrazine (1.0 g, 15 mmole) was added and the mixture was refluxed for 1 hr more. Following the usual work-up, the base was isolated as a yellow-orange oil. The oil was dissolved in ethanol (30 ml) and treated dropwise with 0.90 equiv (27.8 ml) of 1 M phosphoric acid in ethanol. The phosphate salt separated initially as a gum, but dilution with ether (300 ml), seeding, and thorough trituration for several hours gave a uniform yellow solid, 11.5 g (90%), mp 163°–166°. Crystallization of the crude phosphate from methanol-ethanol-ether (1:1:2) afforded 82% recovery of product; mp 163°–166°.

Anal. Calcd. for $C_{18}H_{27}N_3O_2 \cdot H_3PO_4$: C, 52.04; H, 7.28; N, 10.11; P, 7.46. Found, C, 51.95; H, 7.11; N, 10.18; P, 7.71.

EXAMPLE 20.
8-(4-Amino-1-methylbutylamino)-5,6-methylenedioxy-4-methyl-quinoline A. 8-Amino-5,6-methylenedioxy-4-methylquinoline.

4-Amino-1,2-methylenedioxy-5-nitrobenzene was made according to the method of Lott, et al.—J. Amer. Chem. Soc., 70, 3621 (1848). It was subjected to a Skraup reaction with methyl vinyl ketone to provide 5,6-methylenedioxy-4-methyl-8-nitroquinoline. The crude compound was crystallized from acetone to give a 63% yield of pure substance; mp 183°–185°.

Anal. Calcd. for $C_{11}H_8N_2O_4$: C, 56.90; H, 3.47; N, 12.06. Found: C, 57.16; H, 3.50; N, 12.14.

The foregoing nitro compound was reduced after the manner in Example 17A. Following crystallization from cyclohexane, the requisite 8-amino-5,6-methylenedioxy-4-methylquinoline was obtained in 89% yield; mp 118°–120°.

Anal. Calcd. for $C_{11}H_{10}N_2O_2$: C, 65.33; H, 4.98; N, 13.85. Found: C, 64.67; H, 4.99; N, 13.86.

B.
4-Methyl-5,6-methylenedioxy-8-(4-phthalimido-1-methylbutylamino) quinoline Hydrochloride.

A mixture of the above 8-aminoquinoline (10.0 g, 0.049 mole), 1-iodo-4-phthalimidopentane (IPP, 16.98 g, 0.049 mole), triethylamine (5.0 g, 0.049 mole) and 2-ethoxyethanol (10 ml) was heated with stirring at 110° for 2 hr. The reaction mixture was then treated with an additional quantity of IPP (16.98 g) and triethylamine (5.0 g) and kept at 110° for 2 hr. The reaction mixture was cooled and dissolved in chloroform. The chloroform solution was washed with 10% aqueous KOH, dried and concentrated to dryness to give a dark syrup. The syrup was dissolved in ether (800 ml) and insoluble material was removed by filtration. The ethereal solution was treated with ethereal HCl with stirring. The resulting red solid was collected by filtration. Recrystallization from ethanol afforded 16.0 g (71%) of the desired compound; mp 110°–112° (effervescence at 105°).

Anal. Calcd. for $C_{24}H_{23}N_3O_4 \cdot HCl$: C, 63.50; H, 5.33; N, 9.25; Cl, 7.81. Found: C, 63.75; H, 5.44; N, 9.48; Cl, 7.75.

C.
8-(4-Amino-1-methylbutylamino)-5,6-methylenedioxyl-4-methylquinoline Phosphate.

A solution of the above phthalimido intermediate (free base, 12.0 g, 0.029 mole) ethanol (180 ml) containing hydrazine hydrate (75%, 3.9 ml) was heated at reflux for 4 hr. The mixture was concentrated to dryness and the residual solid was shaken with chloroform and 20% aqueous KOH. The chloroform phase was washed with water (x2), dried ($K_2CO_3$) and concentrated to dryness. The resulting free base (8.0 g) was dissolved in ethanol-water (5:1, 90 ml) and 1 M $H_3PO_4$ in ethanol (27 ml) was added dropwise with stirring to give a red gum which crystallized on warming. The solid was recrystallized from ethanol-water (5:1) to afford 5.0 g (50%) of the title compound; mp 185°–187° (shrinking at 182°).

Anal. Calcd. for $C_{16}H_{21}N_3O_2 \cdot H_3PO_4$: C, 49.87; H, 6.27; N, 10.90; P, 8.03. Found: C, 49.85; H, 6.20; N, 11.10; P, 7.93.

EXAMPLE 21.
8-(6-Diethylaminohexylamino)-5-fluoro-6-methoxy-4-methylquinoline A. 8-Amino-5-fluoro-6-methoxy-4-methylquinoline.

2-Fluoro anisole was nitrated according to the method of Elderfield, et al. [J. Amer. Chem. Soc., 68, 1584 (1946)]. The nitro compound was then reduced to 4-amino-2-fluoro anisole [G. Schiemann and T. Miau, Ber., 66, 1179 (1933)], which was acetylated, and further nitrated (cf. Elderfield, et al., loc. cit.) to give 4-acetamido-2-fluoro-5-nitroanisole. Hydrolysis with ethanolic hydrochloric acid (cf. Elderfield, et al., loc. cit.) provided the needed amino compound; mp 145°–147° (from ethanol).

The intermediate 4-amino-2-fluoro-5-nitroanisole and methyl vinyl ketone were subjected to a Skraup reaction. A 32% yield of crude 5-fluoro-6-methoxy-4-methyl-8-nitroquinoline resulted. It was obtained in pure form by recrystallization from ethyl acetate. The recovery was 73% of product which melted 142°–144°.

8-Amino-5-fluoro-6-methoxy-4-methylquinoline was prepared by reduction of the foregoing nitro compound after the method used in Example 9A. A 75% yield resulted. That material was crystallized from ethanol to give 50% recovery of analytically pure compound; mp 126°–128°.

Anal. Calcd. for $C_{11}H_{11}FN_2O$: C, 64.07; H, 5.38; F, 9.21; N, 13.58. Found: C, 64.12; H, 5.40; F, 9.31; N, 13.54.

B.
8-(6-Diethylaminohexylamino)-5-fluoro-6-methoxy-4-methylquinoline Dihydrochloride.

A stirred mixture of 22.4 g (0.109 mole) of 8-amino-5-fluoro-6-methoxy-4-methylquinoline and 35.2 g (0.149 mole) of 6-diethylaminohexylbromide hydrobromide was heated in an oil bath (132°) for 45 minutes while 64.3 g (0.635 mole) of triethylamine was added dropwise. The temperature of the oil bath was maintained at 132° for 3.25 hrs then at 150° for 1 hr. The mixture was cooled to room temperature then diluted with 300 ml of acetone. The solid which separated was collected on a filter, dried, then dissolved in 500 ml of 10% potassium hyroxide. The solution was extracted with ether (3×750 ml). The extracts and the acetone filtrate were combined then concentrated in vacuo to an oil (52 g.) Additional material (3 g) was obtained from a scouting run. The combined material (55 g) was purified by chromatography on a column of silica gel (1 kg) using ethyl acetate then acetone as the eluents. The fractions containing pure product were combined then concentrated in vacuo to an oil; yield 28.1 g (48.7%).

A solution of 28.1 g (0.0779 mole) of 8-(6-diethylaminohexylamino)-5-fluoro-6-methoxy-4-methylquinoline in ether (1.0 l) was dried over anhydrous magnesium sulfate then saturated with anhydrous hydrogen chloride. The gummy solid which separated was collected then recrystallized from ethanol-ether (2:5) (1.4 l); yield 27.3 g (80.8% recovery); mp 263°–269°.

Anal. Calcd. for $C_{21}H_{31}FN_3O.2HCl$: C, 58.20; H, 7.67; Cl, 16.36; F, 4.38; N, 9.70. Found: C, 58.14; H, 7.60; Cl, 16.03; F, 4.22; N, 9.46.

EXAMPLE 22.
8-(4-Amino-1-methylbutylamino)-6-fluoro-4-methylquinoline

A. 8-Amino-6-fluoro-4-methylquinoline.

A Skraup reaction was run with 4-fluoro-2-nitroaniline and methyl vinyl ketone. The crude product was recrystallized multiply from benzene to obtain a 39% yield of pure 6-fluoro-4-methyl-8-nitroquinoline; mp 139°–141°.

Anal. Calcd. for $C_{10}H_7FN_2O_2$: C, 58.25; H, 3.43. Found: C, 58.28; H, 3.49.

The intermediate nitro compound was reduced after the manner described in Example 4A. An 88% yield of product resulted; mp 99°–101°. It was sublimed in vacuo to obtain pure white crystals of 8-amino-6-fluoro-4-methylquinoline; mp 100°–101°. The lower-melting material was satisfactory for use in the next step.

Anal. Calcd. for $C_{10}H_9FN_2$: C, 68.17; H, 5.15; F, 10.79; N, 15.90. Found: C, 68.36; H, 5.04; F, 10.86; N, 16.06.

B.
6-Fluoro-4-methyl-8-(1-methyl-4-phthalimidobutylamino) quinoline.

A stirred mixture of 11.6 g (0.066 mole) of the above amino compound and 20 g (0.067 mole) of 4-bromo-1-phthalimidopentane was maintained at 150° while 10 ml of triethylamine was added dropwise during 2 hr. The mixture was then stirred at 150° for two more hours. This sequence (addition of 20 g of 4-bromo-1-phthalimidopentane in a single portion, dropwise addition of 10 ml of triethylamine during 2 hr and stirring at 150° for two more hours) was repeated three times. The mixture was allowed to cool, diluted with acetone and filtered to remove triethylamine hydrobromide. The filtrate was concentrated and the resulting brown syrup was dissolved in chloroform, washed sequentially with 10% NaOH and water and dried ($K_2CO_3$). The solution was treated with charcoal, passed through a silica column and distilled to give 15.9 g (62%) of phthalimido compound, bp 246°–250°/0.15 mm; mp 58°. This material was used without further purification.

C.
8-(4-Amino-1-methylbutylamino)-6-fluoro-4-methylquinoline Monophosphate.

A mixture of 15.9 g (0.045 mole) of phthalimido compound, 25 ml of 95% hydrazine, 50 ml of chloroform and 500 ml of ethanol was heated under reflux for 3 hr and filtered. The filtrate was concentrated and the residual oil was diluted with 360 ml of ether. The ethereal solution was washed with 30% KOH and extracted with 20% HCl. After washing with ether, the red, acid extract was basified with 30% KOH. The yellow oil was extracted with $Et_2O$ and the extract was dried ($K_2CO_3$) and concentrated. Distillation of the concentrate provided 8.8 g (83%) of free base, bp 142°–168°/0.14 mm. A solution of 1.3 g (0.005 mole) of this material in 20 ml of ethanol was treated with a solution of 1.29 g of 86% $H_3PO_4$ in 10 ml of ethanol. The orange crystals were washed with ether and recrystallized from ethanol (charcoal) to give 1.4 g of monophosphate as a pale yellow crystals with an indefinite melting point (starts to melt at 158° and finally decomposes at 216°).

Anal. Calcd. for $C_{15}H_{20}FN_3.H_3PO_4$: C, 50.14; H, 6.46; N, 11.70; P, 8.62. Found: C, 50.55; H, 6.13; N, 11.55; P, 8.35.

D.
8-(4-Amino-1-methylbutylamino)-6-fluoro-4-methylquinoline Citrate.

Hydrazinolysis of 3 g of phthalimido intermediate (Example 22b, above) and workup in the usual manner (crystallization from ethanol and ether) gave 1.5 g (43%) of the citrate with a melting range of 112°–140°.

Anal. Calcd. for $C_{15}H_{20}FN_3.C_6H_8O_7$: C, 55.62; H, 6.23; F, 4.19; N, 9.27. Found: C, 55.42; H, 6.33; F, 4.29; N, 9.18.

EXAMPLE 23.
8-[2-Hydroxy-2-methyl-3-(2-propylamino)-propylamino]-6-methoxy-4-methylquinoline

A. 3-Chloro-2-methyl-1-(2-propylamino)propan-2-ol hydrochloride

Interaction of 2-chloromethyl-2-methyloxiran and 2-propylamine in ethanol produced the desired compound in 64% yield; mp 180°–182°. It separated well from absolute ethanol as white crystals which melted 180°–182°.

Anal. Calcd. for $C_7H_{16}NO.HCl$: C, 50.44; H, 10.28; Cl, 21.27; N, 8.40. Found: C, 50.50; H, 9.96; Cl, 21.28; N, 8.47.

B.
8-[2-Hydroxy-2-methyl-3-(2-propylamino)-propylamino]-6-methoxy-4-methylquinoline Dihydrochloride.

A stirred mixture of 10.7 g (0.057 mole) of 8-amino-6-methoxy-4-methylquinoline and 11.7 g (0.057 mole) of 3-chloro-2-methyl-1-(2-propylamino)propan-2-ol, hydrochloride was heated in an oil bath (150°) for 1 hr while 5.8 g (0.057 mole) of triethylamine was added, dropwise. The reaction mixture was stirred at 150° for 24 hrs, cooled, basified with 30 ml of 5% aqueous sodium hydroxide, then extracted with dichloromethane (3×100 ml). The organic extracts were combined, washed with water (2×200 ml), dried over anhydrous magnesium sulfate, then concentrated in vacuo to 50 ml. The solution was chromatographed on a column (60 cm×7.5 cm) of silica gel (2.5 kg; activity III) using dichloromethane (10 l) followed by methanol-concentrated ammonium hydroxide (25:1) (7 l) as the eluent. The fractions (1 l each) 13-18 were combined then concentrated in vacuo to an oil. The oil was dissolved in ether (100 ml), and the solution was washed with water (2×200 ml), dried over anhydrous magnesium sulfate, then saturated with anhydrous hydrogen chloride. The solid that separated was collected on a filter, dried, then recrystallized from 300 ml of absolute ethanol; yield 4.6 g; mp 232°-234°, dec.

Anal. Calcd. for $C_{18}H_{29}Cl_2N_3O_2$: C, 55, 38; H, 7.49; Cl, 18.16; N, 10.76. Found: C, 55.33; H, 7.87; Cl, 17.88; N, 10.56.

EXAMPLE 24.
8-(5-Amino-1-methylpentylamino)-6-methoxy-4-methylquinoline.

A. 5-Bromo-1-phthalimidohexane.

A mixture of 1,5-dibromohexane (21.6 g, 0.09 mole) in acetone (75 ml) containing potassium phthalimide (12.3 g, 0.066 mole) was heated at reflux for 24 hr. The mixture was cooled, filtered and concentrated. The excess dibromide was recovered (6.3 g) via distillation at 1.5 mm, 130° internal temperature, and recycled. The total yield of crude product was 20.6 g (74%), mp 48°-51°. This material was used as such in the next step.

B.
6-Methoxy-4-methyl-8-(5-phthalimido-1-methylpentylamino) quinoline.

8-Amino-6-methoxy-4-methylquinoline (5.5 g, 0.03 mole), the above bromophthalimidohexane (8.2 g, 0.26 mole) and diisopropylamine (2.55 g) were dissolved in a mixture ethanol (4.3 ml) and 2-ethoxyethanol (4.3 ml). This solution was heated in a sealed tube at 150° for 3.5 hr. After cooling, the reaction mixture was diluted with ether (400 ml). Diisopropylamine hydrobromide was removed by filtration and the filtrate was concentrated to dryness. The residue crystallized upon trituration with EtOH (50 ml) to give the title compound (5.2 g, 47%), contaminated with a trace amount of starting material. Additional starting 8-aminoquinoline could be recovered from the ethanol filtrate.

C.
8-(5-Amino-1-methylpentylamino)-6-methoxy-4-methylquinoline Diphosphate.

A solution of the above phthalimidoquinoline (10 g, 0.024 mole) in ethanol (400 ml) containing 75% hydrazine hydrate (3.35 ml, 0.036 mole) was heated at reflux for 17 hr. The mixture was concentrated to dryness and the residue was shaken with chloroform and 20% aqueous KOH. The organic layer was dried ($K_2CO_3$) and concentrated to dryness. The residual oil (ca. 8 g) was dissolved in ether (250 ml) and 1 M $H_3PO_4$ in ethanol (50 ml) was added with stirring. The solid was filtered and crystallized from 10% aqueous ethanol (350 ml) to give the 8-(5-amino-1-methylpentylamino)-6-methoxy-4-methylquinoline diphosphate as a dihydrate (9.5 g, 75%), mp 154°-156°, with slow effervescence.

Anal. Calcd. for $C_{17}H_{25}N_3O.2H_3PO_4.2H_2O$: C, 39.31; H, 6.79; N, 9.09; P, 11.93. Found: C, 39.40; H, 6.69; N, 7.82; P, 12.12.

EXAMPLE 25.
8-(6-Aminohexylamino)-6-methoxy-4-methylquinoline.

A.
6-Methoxy-4-methyl-8-(6-phthalimidohexylamino)-quinoline.

A stirred mixture of 20.9 g (0.111 mole) of 8-amino-6-methoxy-4-methylquinoline and 34.5 g (0.111 mole) of N-(6-bromohexyl)phthalimide was heated in an oil bath (130°) while 11.2 g (15.4 ml; 0.111 mole) of triethylamine was added dropwise over a period of 45 minutes. The temperature of the bath was kept at 130° for 60 minutes, at 150° for 60 minutes, between 150° and 190° for 30 minutes, and at 190° for 30 minutes. The mixture was cooled then diluted with acetone (100 ml). The precipitate as collected on a filter, washed with acetone (2×50 ml), dried, then discarded. The filtrate was concentrated in vacuo to a dark oil; yield 53 g. The oil was dissolved in 100 ml of dischloromethane, and the solution was chromatographed on a column (40 cm×8 cm dia) of silica gel (1000 g; activity III) using dichloromethane (1.5 l) as the eluent. Fractions containing the product were combined then concentrated in vacuo; yield 35.5 g (83.7%). That material was satisfactory for conversion to the target compound, however a 93% recovery of analytically pure material (mp 84°-85°) could be obtained by crystallization from ethanol.

Anal. Calcd. for $C_{25}H_{27}N_3O_3$: C, 71.92; H, 6.52; N, 10.06. Found: 71.84; H, 6.77;, N, 10.17.

B.
8-(6-Aminohexylamino)-6-methoxy-4-methylquinoline Dihydrochloride.

The above-described phthalimido compound was subjected to cleavage with hydrazine and the resulting oily product subjected to chromatography on silica (eluants were methylene chloride and a 25:1 mixture of methanol and conc. ammonium hydroxide). The residues from the eluates were dissolved in ethanol, treated with conc. HCl, and concentrated in vacuo to give a 93% yield of crude product. It was recrystallized from ethanol to provide pure 8-(6-aminohexylamino)-6-methoxy-4-methylquinoline dihydrochloride; mp 130°-132°.

Anal. Calcd. for $C_{17}H_{25}N_3O.2HCl$: C, 56.67; H, 7.55; Cl, 19.68; N, 11.66; O, 4.44. Found: C 56.59; H, 7.93; Cl 19.37; N, 11.51; O, 4.71.

EXAMPLE 26.
6-Methoxy-8-[6-(2-methyl-1-propylamino)hexylamino]-4-methyl-quinoline

A. 6-Bromo-N-(2-methyl-1-propyl)hexanamide.

6-Bromohexanoic acid was converted into the acid chloride in 96% yield by the action of oxalyl chloride in benzene solution. It was distilled at 0.9 mm, bp 68°-71°.

The above acid chloride was interacted with 2-methyl-1-propylamine in dry ether. A quantitative yield of crude amide resulted. It was distilled, and the cut boiling 135°-140° (0.35 mm) was taken as the desired compound. The yield was 74%.

B.
6-(6-Methoxy-4-methyl-8-quinolylamino)-N-(2-methyl-1-propyl)hexanamide.

A stirred mixture of 22.6 g (0.120 mole) of 8-amino-6-methoxy-4-methylquinoline and 29.6 g (0.118 mole) of 6-bromo-N-(2-methyl-1-propyl)-hexanamide was heated in an oil bath (130°) while 12.2 g (16.8 ml; 0.120 mole) of triethylamine was added dropwise over 30 minutes. The temperature of the bath was kept at 130° for 30 minutes, at 150° for 60 minutes, between 150° and 190° for 30 minutes, and at 190° for 30 minutes. The mixture was cooled to room temperature then diluted with 25 ml of ethyl acetate. The solid that separated was collected on a filter, extracted with boiling ethyl acetate (3×100 ml), then discarded. The filtrate and extracts were combined, then concentrated in vacuo to a solid; yield 44 g. The solid was dissolved in 130 ml of dichloromethane and purified by elution chromatography on a column (8 cm dia×40 cm) of silica gel (1000 g; activity III) using 1 l of dichloromethane-ether (1:1), followed by 2 l of ether, as eluents. The fractions (100 ml each) containing pure product were combined then concentrated in vacuo. The fractions containing mixtures were concentrated in vacuo then triturated with diethyl ether to yield 25.4 g (60.2%) of crude product. The product was suitable for further transformation. Analytically pure compound was readily obtained (84% recovery) by recrystallization from methylene chloride and ether; mp 111°-112°.

Anal. Calcd. for $C_{21}H_{31}N_3O_2$: C, 70.55; H, 8.74; N, 11.75. Found: C, 70.69; H, 8.52; N, 11.79.

C.
6-Methoxy-8-[6-(2-methyl-1-propylamino)hexylamino]-4-methylquinoline Dihydrochloride.

To a stirred, refluxing suspension of 5.80 g (0.153 mole) of lithium aluminum hydride in 200 ml of dry tetrahydrofuran, under a nitrogen atmosphere was added, dropwise, a solution of 25.4 g (0.071 mole) of the amide from unit B (q.v.) in 250 ml of dry tetrahydrofuran during 1.6 hrs. The mixture was heated at reflux for 3 hrs. Excess lithium aluminum hydride was decomposed by adding a mixture of 25 ml of tetrahydrofuran and 25 ml of water. The suspended solids were collected on a filter, washed with ether (2×500 ml), then discarded. The filtrate and washings were combined, concentrated in vacuo and the residual oil was dissolved in 750 ml of ether. The ether solution was dried over anhydrous magnesium sulfate then concentrated in vacuo to an oil; yield 26.9 g. The oil was dissolved in 300 ml of dichloromethane and the solution was chromatographed on a column (8 cm×40 cm) of silica gel (1000 g; activity III) using ethyl acetate (1250 ml) then methanol-concentrated ammonium hydroxide (25:1) (3500 ml) as the eluents. The fractions (200 ml each) 1-3 gave 2.5 g of starting material, fractions 13-18 were combined then concentrated to an oil. The oil was dissolved in ether (750 ml), and the solution was washed with water (2×375 ml), dried over anhydrous magnesium sulfate, then saturated with anhydrous hydrogen chloride. The solid that separated was collected on a filter, dried, then recrystallized twice from 250 ml of ethanol (charcoal); yield 15.7 g; mp 190°-198°. Analyses showed this to be the monohydrate of the desired dihydrochloride.

Anal. Calcd. for $C_{21}H_{33}N_3O.2HCl.H_2O$: C, 58.07; H, 8.59; Cl, 16.30; N, 9.67; O, 7.37. Found: C, 58.06; H, 8.61; Cl, 16.28; N, 9.54; O, 7.33.

EXAMPLE 27.
8-(6-Diethylaminohexylamino)-6-methoxy-4-methylquinoline

A stirred mixture of 110.5 g (0.5870 mole) of 8-amino-6-methoxy-lepidine and 190 g (0.600 mole) of 6-diethylaminohexyl bromide hydrobromide was heated in an oil bath (130°) for 30 minutes while 346.3 g (477 ml; 3.422 moles) of triethylamine was added, dropwise, over period of 2 hrs. The temperature of the bath was kept at 130° for 2.5 hrs then at 150° for 1 hr. The mixture was cooled to room temperature then diluted with 2 l of diethyl ether. The solid that separated was collected on a filter, dried, then dissolved in 2 l of water containing 100 g of potassium hydroxide, and the solution was extracted with ether (4×1 l). The ethereal filtrate and extracts were combined then concentrated in vacuo; yield 251 g. The residue was purified by repeated chromatography on a column (15 cm×15 cm) of silica gel (4×1460 g; activity III) using ethyl acetate as the eluent. The fractions containing pure product were combined then concentrated in vacuo to a pale yellow oil; yield 134.4 g (55.0%).

The oily base was taken up on anhydrous ether and hydrogen chloride gas introduced. A gummy solid resulted. The solid was separated and crystallized from ethanol-ether following a treatment with charcoal. The dihydrochloride of 8-(6-diethylaminohexylamino)-6-methoxy-4-methyl-quinoline was obtained in 91.6% yield. It was further purified by recrystallization from 2propanol; mp 183°-184°.

Anal. Calcd. for $C_{21}H_{31}N_3O.2HCl$: C, 60.57; H, 8.47; N, 10.09; Cl, 10.09. Found: C, 60.45; H, 8.56; N, 10.04; Cl, 10.04.

EXAMPLE 28.
8-(3-Diethylaminopropylamino)-2,4-dimethyl-6-methoxyquinoline A. 8-Amino-2,4-dimethyl-6-methoxyquinoline.

4-Methoxy-2-nitroaniline and 3-penten-2-one were subjected to a Skraup reaction. The crude product was black and gummy, but extractions with boiling ethyl acetate led to isolation of satisfactory 2,4-dimethyl-6-methoxy-8-nitroquinoline. A yellowish solid resulted from treatment of the ethyl acetate liquors with charcoal and concentration in vacuo. The yield of product was 41%; mp 196°-197°. Further crystallizations from ethyl acetate led to pure compound, mp 197°-198°.

Anal. Calcd. for $C_{12}H_{12}N_2O_3$: C, 62.06; H, 5.21; N, 12.06. Found: C, 61.79; H, 6.33; N, 11.82.

Reduction of the nitro compound to 8-amino-2,4-dimethyl-6-methoxy-quinoline was done with tin and tin (II) chloride in concentrated hydrochloric acid at 5°. The product was isolated as the base, which was an off-white solid. A 96% yield of once-crystallized compound (from cyclohexane) was obtained; m.p. 116°-117°. Additional crystallizations from cyclohexane did not raise the melting point.

Anal. Calcd. for $C_{12}H_{14}N_2O$: C, 71.26; H, 6.98; N, 13.85. Found: C, 71.13; H, 6.98; N, 13.74.

B.
8-(3-Diethylaminopropylamino)-2,4-dimethyl-6-methoxyquinoline Diphosphate.

2,4-Dimethyl-6-methoxy-8-aminoquinoline (10.0 g, 0.049 mole) and 3-diethylaminopropyl chloride (11.25 g, 0.075 mole) were heated at 120°–125° for 7 hr. Then additional 3-diethylaminopropyl chloride (3.75 g, 0.025 mole) and triethylamine (2.5 g, 0.025 mole) were added and the solution was maintained at 120°–125° for 17 hr. The product free base was extracted with diethyl ether (4×250 ml), dried (potassium carbonate) and the ether was removed. The resulting residue (13.2 g) was chromatographed over silica gel (5 cm×70 cm column) and eluted with benzene-ether (1:1 v/v). Those fractions which were one-spot by tlc were collected and other product fractions were reworked separately.

The one-spot material (8.2 g) was dissolved and heated in water (25 ml) and ethanol (60 ml) containing 85% phosphoric acid (6.2 g). The hot solution was treated with Norit, filtered (celite) and allowed to cool. The product was collected by filtration, washed with ether and air-dried. The crude diphosphate salt (12.9 g) was recrystallized from methanol-isopropanol-ether to give a first crop, 4.2 g, mp 177°–179°, and a second crop, 3.7 g, mp 176.5°–178°. The combined yield was 7.9 g.

The less pure fractions of base were subjected to column chromatography, converted into phosphate, and crystallized from methanol by addition of ether. The salt had a considerable melting-range, hence was converted to the base, chromatrographed on silica gel, and the phosphate prepared.

All samples of phosphate were combined and crystallized from 83% aqueous ethanol, then dried at 85°/2 mm. The pure diphosphate (38% yield) melted 177°–179.5°.

Anal. Calcd. for $C_{19}H_{29}N_3O.2H_3PO_4$: C, 44.62; H, 6.90; N, 8.22; P, 12.11. Found: C, 44.41; H, 6.93; N, 8.06; P, 12.04.

In summary then, the instant process of this invention comprises the discovery that when 8-NH2quinolines are reacted with a substituted alkyl halide (a chloride, bromide, or iodide) in the presence of an amine acid acceptor having a boiling point of 80°–90° C., a 8-NHR quinoline will be efficiently formed which may be readily separated and purified for use as a chemotherapeutic agent, or as an intermediate to form another chemotherapeutic agent, or for conversion to a pharmaceutically acceptable salt for therapeutic application. The process of this invention may be carried out in the presence of an alcohol solvent if desired.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced herein.

What is claimed and desired to be secured by the United States Letters Patent is:

1. A process for producing anti-parasitic compounds having a formula of:

QNHR wherein Q represents a substituted or unsubstituted 8-quinolyl moiety and R represents an amino or amido substituted alkyl grouping comprising: reacting Q—NH$_2$ with R—X wherein X is a halogen selected from the group consisting of chloride, bromide, and iodide in the presence of a trialkyl or dialkyl amine acid acceptor having a boiling point of from 80°–90° C., wherein the amine acid acceptor is added incrementally during the reaction or both amine acid acceptor and R—X are added incrementally during the reaction, to form QNHR and HX.

2. The process of claim 1 wherein said amine is a member selected from the group consisting of triethylamine and diisopropylamine.

3. The process of claim 1 further comprising reacting QNH$_2$ and RX in the presence of a solvent selected from the group consisting of ethanol and 2-ethoxyethanol.

4. The process of claim 3 further comprising reacting QNH$_2$ and RX in the presence of a solvent comprising a mixture of ethanol and 2-ethoxyethanol.

5. The process of claim 1 wherein R is an amino or amido substituted alkyl grouping containing from 2 to 6 carbon atoms within the alkyl group.

6. The process of claim 1 wherein R-X is a member selected from the group consisting of 1-iodo-4-phthalimidopentane, 1-chloro-4 phthalimidopentane, 4-bromo-1 phthalimidopentane, 2-bromo-5 phthalimidopentane, 4 iodo-1 phthalimidopentane, 1-phthalimido-4 iodohexane, 6-diethylaminohexyl bromide hydrobromide, 3-chloro-2-methyl-1-(2-propylamino) propan-2-ol hydrochloride, 5-bromo-1-phthalimidohexane, N-(6-bromohexyl) phthalimide, 6-bromo-N-(2-methyl-1-propyl)-hexanamide, and 3-diethylaminopropyl chloride.

7. The process of claim 2 wherein said amine is triethylamine.

8. The process of claim 2 wherein said amine is diisopropylamine.

9. The process of claim 1 which is carried out in the presence of a dialkylamine acid acceptor.

10. The process of claim 1 which is carried out in the presence of a trialkylamine acid acceptor.

* * * * *